US005866630A

United States Patent [19]

Mitra et al.

[11] Patent Number: 5,866,630
[45] Date of Patent: *Feb. 2, 1999

[54] OPTIONALLY CROSSLINKABLE COATINGS COMPOSITIONS AND METHODS OF USE

[75] Inventors: Sumita B. Mitra, West St. Paul; Charles E. Shelburne, Brooklyn Park; Sharon M. Rozzi, West Lakeland Township; Brant L. Kedrowski, Minneapolis, all of Minn.

[73] Assignee: Minnesota Mining and Manufacturing Company, St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 472,000

[22] Filed: Jun. 6, 1995

Related U.S. Application Data

[60] Division of Ser. No. 347,861, Dec. 1, 1994, which is a continuation-in-part of Ser. No. 163,028, Dec. 6, 1993, abandoned.

[51] Int. Cl.[6] ............................. A61K 6/00; C08F 30/08
[52] U.S. Cl. ..................... 523/118; 523/115; 524/547; 526/279; 528/33; 528/34; 424/49; 424/78.31
[58] Field of Search ................ 524/547; 523/115, 523/118; 526/279; 424/49, 78.31; 528/33, 34

[56] References Cited

U.S. PATENT DOCUMENTS

| | | | |
|---|---|---|---|
| 4,161,518 | 7/1979 | Wen et al. | 424/52 |
| 4,663,202 | 5/1987 | Causton | 427/388 |
| 4,693,935 | 9/1987 | Mazurek | 428/352 |
| 4,728,571 | 3/1988 | Clemens et al. | 428/352 |
| 4,872,936 | 10/1989 | Engelbrecht | 156/307.3 |
| 4,950,479 | 8/1990 | Hill et al. | 424/49 |
| 4,972,037 | 11/1990 | Garbe et al. | 526/245 |
| 4,981,902 | 1/1991 | Mitra et al. | 524/547 |
| 4,981,903 | 1/1991 | Garbe et al. | 524/547 |
| 4,985,155 | 1/1991 | Yamada et al. | 452/8.6 |
| 5,021,477 | 6/1991 | Garbe et al. | 424/70 |
| 5,032,387 | 7/1991 | Hill et al. | 424/49 |
| 5,032,455 | 7/1991 | Dana et al. | 428/394 |
| 5,078,988 | 1/1992 | Lin et al. | 424/49 |
| 5,086,107 | 2/1992 | Arai et al. | 524/424 |
| 5,154,762 | 10/1992 | Mitra et al. | 106/35 |
| 5,188,822 | 2/1993 | Viccaro et al. | 424/52 |
| 5,219,899 | 6/1993 | Panster et al. | 523/115 |
| 5,244,696 | 9/1993 | Hazan et al. | 427/402 |
| 5,322,890 | 6/1994 | Ando et al. | 524/806 |
| 5,405,888 | 4/1995 | Takeoka | 528/32 |

FOREIGN PATENT DOCUMENTS

| | | |
|---|---|---|
| 0412770 | 2/1991 | European Pat. Off. . |
| 0412771 | 2/1991 | European Pat. Off. . |
| 0528457 | 2/1993 | European Pat. Off. . |
| 1104786 | 10/1965 | United Kingdom . |
| WO 91/13608 | 3/1991 | WIPO . |
| WO 9323009 | 11/1993 | WIPO . |

OTHER PUBLICATIONS

A. Gaffar, J. Afflitto, N. Nuran, "Toothbrush Chemistry" Am. Chem. Soc. (Jul. 1993), International Search Report.

*Primary Examiner*—Andrew E. C. Merriam
*Attorney, Agent, or Firm*—Dale A. Bjorkman

[57] ABSTRACT

Coatings for hard tissue and surfaces of the oral environment are provided that reduce adhesion of bacteria and proteinaceous substances to these surfaces. Methods of reducing adhesion of these materials to such surfaces, and polymers for incorporation into such coatings are also provided.

20 Claims, 3 Drawing Sheets

OPTIONALLY CROSSLINKABLE COATINGS COMPOSITIONS AND METHODS OF USE

CROSS-REFERENCE TO RELATED APPLICATION

This application is a divisional application of U.S. Ser. No. 08/347,861, filed Dec. 1, 1994, now pending, which is a continuation-in-part, application of U.S. application Ser. No. 08/163,028 filed Dec. 6, 1993, now abandoned.

FIELD OF INVENTION

This invention relates to coatings on hard tissue surfaces or surfaces of the oral environment. More specifically, this invention relates to substantive coatings for hard tissue surfaces or surfaces of the oral environment.

BACKGROUND OF THE INVENTION

Plaque is a common factor in caries, gum disease and discoloration of teeth and greatly contributes to their development. Plaque is initiated when cariogenic bacteria adhere to pellicle, a proteinaceous film on the surface of teeth. Plaque, in turn, acts as a nucleus for the formation of calculus. As calculus matures and hardens it tends to stain due to the absorption of dietary chromagens. Additionally, oral restorative materials may be inherently susceptible to build-up of stain from dietary chromagens. It is desirable to have a means to avoid stain absorption and adherence of bacteria to hard tissue and surfaces of the oral environment.

Silicone oils, because of their hydrophobic nature, have been suggested for inclusion in dentrifices to inhibit the staining process. However their adhesion and retention on tooth surfaces is typically quite low.

U.S. Pat. No. 5,078,988 to Lin et al. discloses dentifrices including modified aminoalkyl silicones. The modified silicones are said to form a hydrophobic layer on the teeth for prevention of caries and stain. PCT patent application No. WO 91/13608 to Rolla et al. discloses dentifrices comprising a liquid silicone oil and a fat-soluble antibacterial agent, which is described as being useful for protection of teeth against plaque formation due to a slow release of antibacterial agent into the saliva.

U.S. Pat. No. 4,981,903 to Garbe et al. discloses pressure-sensitive or non-pressure sensitive adhesive compositions comprising a vinyl polymeric backbone with grafted pendant siloxane polymeric moieties. These compositions are disclosed to be useful as good topical application binding materials for application in cosmetics and medicaments, and also as sealant compositions for porous materials such as paper and wood. See col. 3, lines 25 through 31. U.S. Pat. No. 4,972,037 to Garbe et al. discloses compositions useful as an adhesive at room temperature which comprise a copolymer having both pendant fluorochemical groups and pendant polysiloxane grafts. These compositions are also useful in topical applications, including the application of cosmetics and medicaments and for sealant compositions for porous materials such as paper and wood. See col. 3, lines 25 through 33. U.S. Pat. No. 4981,902 to Mitra, et. al. discloses non-pressure-sensitive adhesive acrylate or methacryate polymers having pendant polysiloxane grafts. The polymers comprise monomers having polar functionality, and are described as useful in coating compositions for animal bodies.

U.S. Pat. No. 4,693,935 to Mazurek discloses pressure-sensitive adhesive compositions comprising a copolymer having a vinyl polymeric backbone having grafted thereto polysiloxane moieties. U.S. Pat. No. 4,728,571 to Clemens et al. discloses release coating compositions comprising polysiloxane grafted copolymer and blends thereof on sheet materials.

SUMMARY OF THE INVENTION

The present invention provides coatings on hard tissue surfaces or surfaces of the oral environment, which coating comprises a polymer comprising repeating units A) 1–80% by weight of a polar or polarizable group
B) 0–98% by weight of a modulating group
C) 1–40% by weight of a hydrophobic graft polysiloxane chain having molecular weight of at least 500.

The present invention also provides dental compositions suitable for coating human oral surfaces comprising a polymer comprising repeating units A) 1–80% by weight of a polar or polarizable group
B) 0–98% by weight of a modulating group
C) 1–40% by weight of a hydrophobic graft polysiloxane chain having molecular weight of at least 500, wherein said polymer additionally contains at least one silane moiety that is capable of undergoing a condensation reaction.

These compositions optionally may also comprise catalysts to promote the silane condensation reaction, and optionally an additional compound comprising at least two condensation silicone reaction sites that are capable of undergoing a condensation reaction. This additional compound acts as a bridging compound between the polymers described above after completion of the condensation reaction.

Additionally, it has surprisingly been found that significant enhancement of resistance to stain and bacterial adhesion may be provided by treatment of surfaces having the above coating with a surfactant.

The present invention also provides in another embodiment polymers for coating hard tissue surfaces or surfaces of the oral environment that are crosslinkable on the surface.

In yet another embodiment, dental devices are provided that have a coating comprising the polymer system as noted above.

DETAILED DESCRIPTION

Figure 1:
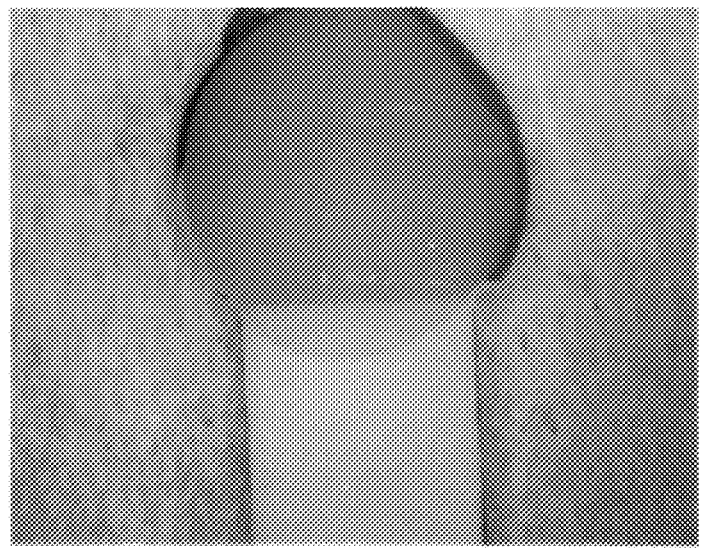
FIG. 1 is a photograph of a tooth chip having a coating of the present invention applied thereto, which shows no retention of a dye to the tooth material.

This invention relates to coatings on hard tissues such as dentin, enamel, cementum and bone. Alternatively, the coating may be provided on other surfaces of the oral environment, including surfaces of dental restorations, orthodontic devices or prostodontic devices. Dental restorations include restorations fabricated from resin-based composites, amalgam, glass ionomers, ceramics and a variety of hybrid materials derived from these. Orthodontic devices include orthodontic brackets, wires and the like. Prostodontic devices include dental bridges, crowns, dentures, and the like.

The coatings are provided in an amount sufficient to provide resistance of the coated surface to bacterial adhesion, plaque formation or staining from foods or dyes. The coating may be provided as a continuous or semi-continuous layer. Preferably, the coating is applied in an amount at least sufficient to provide a substantially continuous monolayer of polymer as described herein on the coated surface.

The coatings provided in accordance with the invention are highly substantive to the aforementioned surfaces. The coatings have low frictional coefficients and have high resistance to plaque, bacteria, food stains and the like.

It has surprisingly further been discovered that when a surface having a coating as described herein is treated with a composition comprising a surfactant, enhanced resistance to adhesion of bacteria and proteinaceous substances on the surface is observed. The surfactant-treatment step provides this surprising benefit even if the coated surface is exposed to bacteria and proteinaceous substances before the surfactant-treatment step. Thus, a coating as described herein that has been treated with a surfactant-containing composition is apparently physically different from coatings that have not been treated with a surfactant-containing composition. While not being bound by theory, it is believed that the surfactant treatment orients the polysiloxane component of the polymer of the coating, thereby enhancing the bacteria adhesion and stain resistant properties of the coating.

The surfactant treatment can be applied (i) as part of the initial coating (ii) subsequent to initial coating, but before exposing the coated surface to undesirable oral organisms of proteinaceous substances, or (iii) after exposing the coated surface to bacteria and the like. In the last case, the surfactant treatment can be reapplied from time to time.

The coating of the present invention comprises a vinylic copolymer having repeat units of A, B and C, where A is derived from an ethylenically unsaturated monomer containing at least one polar or polarizable group, B is derived from an ethylenically unsaturated monomer optionally containing modifying groups and C is derived from an ethylenically unsaturated organosiloxane chain. Preferably, the polymer is less than 0.1% soluble in water.

More specifically, the unit A is derived from vinylic monomers such as acrylates, methacrylates, crotonates, itaconates and the like. The polar groups can be acidic, basic or salt. These groups can also be ionic or neutral.

Examples of polar or polarizable groups include neutral groups such as hydroxy, thio, substituted and unsubstituted amido, cyclic ethers (such as oxanes, oxetanes, furans and pyrans), basic groups (such as phosphines and amines, including primary, secondary, tertiary amines), acidic groups (such as oxy acids, and thiooxyacids of C, S, P, B) and ionic groups (such as quarternary ammonium, carboxylate salt, sulfonic acid salt and the like) and the precursors and protected forms of these groups. Additionally, A could be a macromonomer. More specific examples of such groups follow.

The A units may be derived from mono- or multifunctional carboxyl group containing molecules represented by the general formula:

$$CH_2=CR^2G-(COOH)_d$$

where $R^2$=H, methyl, ethyl, cyano, carboxy or carboxymethyl, d=1–5 and G is a bond or a hydrocarbyl radical linking group containing from 1–12 carbon atoms of valence d+1 and optionally substituted with and/or interrupted with a substituted or unsubstituted heteroatom (such as O, S, N and P). Optionally, this unit may be provided in its salt form. The preferred monomers in this class are acrylic acid, methacrylic acid, itaconic acid and N-acryloyl glycine.

The A units may, for example, be derived from mono- or multifunctional hydroxy group containing molecules represented by the general formula:

$$CH_2=CR^2-CO-L-R^3-(OH)_d$$

where $R^2$=H, methyl, ethyl, cyano, carboxy or carboxyalkyl, L=O, NH, d=1–5 and $R^3$ is a hydrocarbyl radical of valence d+1 containing from 1–12 carbon atoms. The preferred monomers in this class are hydroxyethyl (meth)acrylate, hydroxypropyl (meth)acrylate, hydroxybutyl (meth)acrylate, glycerol mono(meth)acrylate, tris(hydroxymethyl)ethane monoacrylate, pentaerythritol mono (meth)acrylate, N-hydroxymethyl (meth)acrylamide, hydroxyethyl (meth)acrylamide and hydroxypropyl (meth)acrylamide.

The A unit may alternatively be derived from mono- or multifunctional amino group containing molecules of the general formula:

$$CH_2=CR^2-CO-L-R^3-(NR^4R^5)_d$$

where $R^2$, L, $R^3$, and d are as defined above and $R^4$ and $R^5$ are H or alkyl groups of 1–12 carbon atoms or together they constitute a carbocyclic or heterocyclic group. Preferred monomers of this class are aminoethyl (meth)acrylate, aminopropyl (meth)acrylate, N,N-dimethylaminoethyl (meth)acrylate, N,N-diethylaminoethyl (meth)acrylate, N,N-dimethylaminopropyl (meth)acrylamide, N-isopropylaminopropyl (meth)acrylamide and 4-methyl-1-acryloyl-piperazine.

The A unit may also be derived from alkoxy substituted (meth)acrylates or (meth)acrylamides such as methoxyethyl (meth)acrylate, 2(2-ethoxyethoxy)ethyl (meth)acrylate, polyethylene glycol mono(meth)acrylate or polypropylene glycol mono(meth)acrylate.

A units may be derived from substituted or unsubstituted ammonium monomers of the general formula:

$$CH_2=CR^2-CO-L-R^3-(\overset{\oplus}{NR^4R^5R^6})_dQ^-$$

where $R^2$, $R^3$, $R^4$, $R^5$, L and d are as defined above, and where $R^6$ is H or alkyl of 1–12 carbon atoms and $Q^-$ is an organic or inorganic anion. Preferred examples of such monomers are 2-N,N,N-trimethylammonium ethyl (meth)acrylate, 2-N,N,N-triethylammonium ethyl (meth)acrylate, 3-N,N,N-trimethylammonium propyl (meth)acrylate, N(2-N',N',N'-trimethylammonium) ethyl, (meth)acrylamide, N-(dimethyl hydroxyethyl ammonium)propyl (meth)acrylamide etc. where the counterion may be flouride, chloride, bromide, acetate, propionate, laurate, palmitate, stearate etc. The monomer can also be N,N-dimethyl diallyl ammonium salt of an organic or inorganic counterion.

Ammonium group containing polymers can also be prepared by using as the A unit any of the amino group containing monomer described above, and acidifying the resultant polymers with organic or inorganic acid to a pH where the pendant amino groups are substantially protonated. Totally substituted ammonium group containing polymers may be prepared by alkylating the above described amino polymers with alkylating groups, the method being commonly known in the art as the Menschutkin reaction.

The A unit of the invention can also be derived from sulfonic acid group containing monomers, such as vinyl sulfonic acid, styrene sulfonic acid, 2-acrylamido-2-methyl propane sulfonic acid, allyloxybenze sulfonic acid, and the like. Alternatively, the A unit may be derived from phosphorous acid or boron acid group-containing monomers. These monomers may be used in the protonated acid form as monomers and the corresponding polymers obtained may be neutralized with an organic or inorganic base to give the salt form of the polymers.

The unit B is derived from acrylate or methacrylate or other vinyl polymerizable starting monomers and optionally contains functionalities that modulate properties such as glass transition temperature, solubility in the carrier medium, hydrophilic-hydrophobic balance and the like.

Examples of unit B monomers include the lower to intermediate methacrylic acid esters of 1–12 carbon straight, branched or cyclic alcohols. Other examples of B unit monomers include styrene, vinyl esters, vinyl chloride, vinylidene chloride, acryloyl monomers and the like.

Further examples of B monomers are acrylic or methacrylic acid esters of 1,1-dihydroperfluoroalkanols (1) and homologs (2), (1) $CF_3(CF_2)_xCH_2OH$ where x is zero to 20 and y is at least 1 up to 10

(2) $CF_3(CF_2)_x(CH_2)_yOH$ (3) w-hydrofluoroalkanols 3, $HCF_2(CF_2)_x(CH_2)_yOH$ where x is 0 to 20 and y is at least 1 up to 10

(4) fluoroalkylsulfonamido alcohols 4, $$CF_3(CF_2)_xSO_2N\begin{matrix}R^1\\ \\CH_2CH_2OH\end{matrix}$$

where x is zero to 20 and $R_1$ is alkyl or arylalkyl of up to 20 carbon atoms or cycloalkyl of up to 6 ring carbon atoms (5) cyclic fluoroalkyl alcohols 5, $$(CF_2)_z\begin{matrix}CF_2\\ \\CF_2\end{matrix}CF\text{-}(CH_2)_yOH$$

where z is zero to 7 and y is at least 1 up to 10

(6) $CF_3(CF_2CF_2\text{—O})_q(CF_2O)_x(CH_2)_yOH$ where q is 2 to 20 and greater than x, x is 0 to 20, and y is at least 1 up to 10

$$CF_3(CF_2)_rO\text{—}\left(\begin{matrix}CF_3\\|\\C\text{—}CF_2\text{—O}\\|\\F\end{matrix}\right)_p\text{—}(CH_2)_sOH$$

where p and s are at least 1 and r is 1 to 6

Preferred polymerized A monomer backbone compositions include polymers of fluoroacrylates 8–13.

(8)
$$C_7F_{15}CH_2OCCH=CH_2$$
with C=O (9)
$$C_7F_{15}CH_2OCC(CH_3)=CH_2$$
with C=O (10)

[perfluorocyclohexyl structure with $CH_2OCCH=CH_2$ group]

(11)
$$C_8F_{17}SO_2N\begin{matrix}CH_2CH_2CH_2CH_3\\ \\CH_2CH_2OCCH=CH_2\end{matrix}$$
with C=O

(12)
$$C_8F_{17}SO_2N\begin{matrix}CH_2CH_3\\ \\CH_2CH_2OCCH(CH_3)=CH_2\end{matrix}$$
with C=O

(13)
$$C_4F_9O(CF(CF_3)_2\text{—}CF_2\text{—O})_2\text{—}CH_2OCCH=CH_2$$
with C=O B may also optionally be derived from macromonomers such as those derived from styrene, α-methystyrene, vinyl toluene or methyl methacrylate. Preferred such macromonomers have a molecular weight of 500–100,000.

The unit C is derived from an ethylenically unsaturated preformed organosiloxane chain. The molecular weight of this unit is generally above 500.

The unit C of the invention may be derived from a monomer having the general formula $X(Y)_n\text{—}Si(R)_{3-m}Z_m$ wherein X is a vinyl group copolymerizable with the B and B monomers;

Y is a divalent linking group (e.g., alkylene, arylene, alkarylene, and aralkylene of 1 to 30 carbon atoms) and incorporating heteroatoms e.g. O, N, S, P. Examples are ester, amide, urethane, urea groups.

n is zero or 1;

m is an integer of from 1 to 3;

R is hydrogen, lower alkyl (e.g., 1 to 4 carbon atoms, methyl, ethyl, or propyl), aryl (e.g., 6 to 20 carbon atoms, phenyl or substituted phenyl), or alkoxy (preferably lower alkoxy of 1 to 4 carbon atoms);

Z is a monovalent siloxane polymeric moiety having a number average molecular weight above about 500 and is essentially unreactive under copolymerization conditions;

The preferred C monomer may be further defined as having an X group which has the general formula

wherein $R^7$ is a hydrogen atom or a COOH group and $R^8$ is a hydrogen atom, a methyl group, or a $CH_2COOH$ group.

The Z group of the C monomer has the general formula

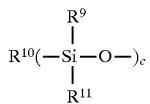

where $R^9$ and $R^{11}$ are independently lower alkyl, aryl, or fluoroalkyl, where lower alkyl and fluoroalkyl both refer to alkyl groups having from one to three carbon atoms and where aryl refers to phenyl or substituted phenyl (of up to 20 carbon atoms). $R^{10}$ may be alkyl (of 1 to 20 carbon atoms), alkoxy (of 1 to 20 carbon atoms), alkylamino (of 1 to 20 carbon atoms), aryl (of up to 20 carbon atoms), hydroxyl, or fluoroalkyl (of 1 to 20 carbon atoms), and e is an integer from about 5 to about 700. Preferably, the C monomer has a general formula selected from the group consisting of the following, where m is 1, 2, or 3, g is zero or 1, R" may be alkyl (of 1 to 10 carbon atoms) or hydrogen, f is an integer from 2 to 6, h is an integer from zero to 2, and X, R, and Z are as defined above:

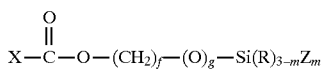

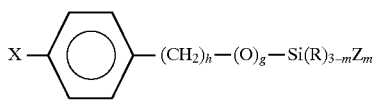

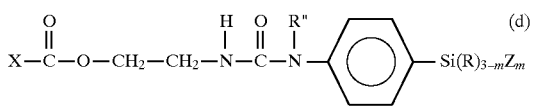

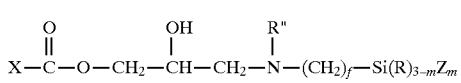

Particularly preferred polymers for use in the present invention have the composition wherein the A group is derived from mono- or multifunctional carboxyl group-containing molecules represented by the general formula:

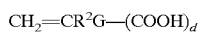

where $R^2$=H or methyl d=1, and

G is a bond or a hydrocarbyl radical linking group containing from 1–12 carbon atoms of valence d+1, or a salt thereof; and the C group is derived from a monomer of the formula

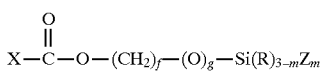

or

wherein

X is a vinyl group copolymerizable with the A and B monomers;

m is an integer of from 1 to 3;

R is hydrogen, lower alkyl;

Z is a monovalent siloxane polymeric moiety having a number average molecular weight above about 500 and is essentially unreactive under copolymerization conditions.

Monomers used to provide the C unit of this invention are terminally functional polymers having a single functional group (vinyl, ethylenically unsaturated, acryloyl, or methacryloyl group) and are sometimes termed macromonomers or "macromers". Such monomers are known and may be prepared by the method disclosed by Milkovich et al., as described in U.S. Pat. Nos. 3,786,116 and 3,842,059. The preparation of polydimethylsiloxane macromonomer and subsequent copolymerization with vinyl monomer have been described in several papers by Y. Yamashita et al., [Polymer J. 14, 913 (1982); ACS Polymer Preprints 25 (1), 245 (1984); Makromol. Chem. 185, 9 (1984)]. This method of macromonomer preparation involves the anionic polymerization of hexamethylcyclotrisiloxane monomer ($D_3$) to form living polymer of controlled molecular weight, and termination is achieved via chlorosilane compounds containing a polymerizable vinyl group. Free radical copolymerization of the monofunctional siloxane macromonomer with vinyl monomer or monomers provides siloxane-grafted copolymer of well-defined structure, i.e., controlled length and number of grafted siloxane branches.

Suitable monomers for use in the above mentioned anionic polymerization are, in general, diorganocyclosiloxanes of the formula

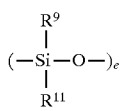

where $R^9$ and $R^{11}$ are as previously defined and where e is an integer of 3 to 7. Preferred are the cyclic siloxanes where e is 3 or 4 and $R^9$ and $R^{11}$ are both methyl, these cyclic siloxanes being hereafter designated $D_3$ and $D_4$, respectively. $D_3$, which is a strained ring structure, is especially preferred.

Initiators of the anionic polymerization are chosen such that monofunctional living polymer is produced. Suitable initiators include alkali metal hydrocarbons such as alkyl or aryl lithium, sodium, or potassium compounds containing up to 20 carbon atoms in the alkyl or aryl radical or more, preferably up to 8 carbon atoms. Examples of such compounds are ethylsodium, propylsodium, phenylsodium, butylpotassium, octylpotassium, methyllithium, ethyllithium, n-butyllithium, sec-butyllithium, tert-butyllithium, phenyllithium, and 2-ethylhexyllithium. Lithium compounds are preferred as initiators. Also suitable as initiators are alkali metal alkoxides, hydroxides, and amides, as well as triorganosilanolates of the formula

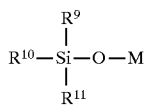

where M is alkali metal, tetraalkylammonium, or tetraalkylphosphonium cation and where $R^9$, $R^{10}$, and $R^{11}$ are as previously defined. The preferred triorganosilanolate initiator is lithium trimethylsilanolate (LTMS). In general, the preferred use of both strained cyclic monomer and lithium initiator reduces the likelihood of redistribution reactions and thereby provides siloxane macromonomer of narrow molecular weight distribution which is reasonably free of unwanted cyclic oligomers.

Molecular weight is determined by the initiator/cyclic monomer ratio, and thus the amount of initiator may vary from about 0.004 to about 0.4 mole of organometallic initiator per mole of monomer. Preferably, the amount will be from about 0.008 to about 0.04 mole of initiator per mole of monomer.

For the initiation of the anionic polymerization, an inert, preferably polar organic solvent can be utilized. Anionic polymerization propagation with lithium counterion requires either a strong polar solvent such as tetrahydrofuran, dimethyl sulfoxide, or hexamethylphosphorous triamide, or a mixture of such polar solvent with nonpolar aliphatic, cycloaliphatic, or aromatic hydrocarbon solvent such as hexane, heptane, octane, cyclohexane, or toluene. The polar solvent serves to "activate" the silanolate ion, making propagation possible.

Generally, the polymerization can be carried out at a temperature ranging from about −50° C. to about 100° C., preferably from about −20° C. to about 30° C. Anhydrous conditions and an inert atmosphere such as nitrogen, helium, or argon are required.

Termination of the anionic polymerization is, in general, achieved via direct reaction of the living polymeric anion with halogen-containing termination agents, i.e., functionalized chlorosilanes, to produce vinyl-terminated polymeric monomers. Such terminating agents may be represented by the general formula $X(Y)_n Si(R)_{3-m}$, $Cl_m$, where m is 1, 2, or 3 and where X, Y, n, and R have been previously defined. A preferred terminating agent is methacryloxypropyldimethylchlorosilane. The termination reaction is carried out by adding a slight molar excess of the terminating agent (relative to the amount of initiator) to the living polymer at the polymerization temperature. According to the aforementioned papers by Y. Yamashita et al., the reaction mixture may be ultrasonically irradiated after addition of the terminating agent in order to enhance functionality of the macromonomer. Purification of the macromonomer can be effected by addition of methanol.

The copolymer used in this invention is conveniently prepared by copolymerizing the starting monomer units A, B and C by standard polymerizing techniques.

The polymer may also contain one or more crosslinkable groups for later fixing of the coating or surface composition by a subsequent crosslinking reaction after the polymer has been placed on the intended substrate. Copolymers where the group B contains a crosslinkable group can be prepared by reacting an electrophilic or nucleophilic moiety of the copolymer with another compound containing the appropriate reactive group and at least one crosslinkable group, such as an ethylenic group or an epoxy group. The electrophilic or nucleophilic moiety can in some cases be the same as that present in unit A of the copolymer.

The present invention therefore also contemplates new polymers comprising repeating units
A) 1–80% by weight of a polar or polarizable group
B) 0–98% by weight of a modulating group
C) 1–40% by weight of a hydrophobic graft polysiloxane chain having molecular weight of at least 500, wherein the polymer additionally comprises pendent crosslinkable groups.

The crosslinkable group is capable of undergoing a free-radical or cationic crosslinking reaction. Suitable crosslinkable groups include, but are not limited to, polymerizable ethylenically unsaturated groups and polymerizable epoxy groups. Ethylenically unsaturated groups are preferred, especially those that can be polymerized by means of a free-radical mechanism, examples of which are substituted and unsubstituted acrylates, methyacrylates, alkenes and acrylamides. In aqueous systems, polymerizable groups that are polymerized by a cationic mechanism, e.g., polymerizable ethylenically unsaturated groups such as vinyl ether groups and polymerizable epoxy groups, are less preferred since a free-radical mechanism is typically easier to employ in such systems than a cationic mechanism.

Crosslinkable polymers can be prepared according to a variety of synthetic routes, including, but not limited to reacting a polymer having electrophilic or neucleophilic groups with less than an one equivalent of a suitable compound in order to form pendent crosslinkable groups, thereby leaving electrophilic or neucleophilic groups unreacted. Alternatively, the appropriate monomers may be copolymerized with a pendent crosslinkable group already present in the monomer. The reaction in this process must be carefully controlled to avoid complete reaction of all groups in the polymerization stage, or the reaction used to form the polymer must be different from the reaction used to form crosslinks between the polymers.

The first synthetic route described above for making the crosslinkable polymer can presently be carried out by the use of a "coupling compound", i.e., a compound containing both a pendent crosslinkable group and a reactive group capable of reacting with the polymer through a functionality existing on a starting material polymer in order to form a covalent bond between the coupling compound and the electrophilic or neucleophilic group, thereby linking the pendent crosslinking group to the backbone of the polymer. Suitable coupling compounds are organic compounds, optionally containing non-interfering substituents and/or non-interfering linking groups between the pendent crosslinking group and the reactive group.

Coupling compounds suitable for use for preparing polymers of the present invention include compounds that contain at least one group capable of reacting with a polar group in order to form a covalent bond, as well as at least one polymerizable ethylenically unsaturated group. When the polar group is carboxyl, a number of groups are capable of reacting with it, including both electrophilic and nucleophilic groups. Examples of such groups include the following moieties, and groups containing these moieties:—OH, —NH$_2$, —NCO, —COCl, and

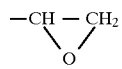

When the attaching site is an alcohol, a number of groups are capable of reacting with the alcohol. Examples of such groups include the following moieties, and groups containing these moieties: —NCO, —COCl,

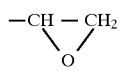

Examples of suitable coupling compounds to attach crosslinkable groups include, for example, acryloyl chloride, methacryloyl chloride, vinyl azalactone, allyl isocyanate, 2-hydroxyethylmethacrylate, 2-aminoethylmethacrylate, and 2-isocyanatoethylmethacrylate. Other examples of suitable coupling compounds include those described in U.S. Pat. No. 4,035,321. Examples of preferred coupling compounds include, for example, the following methacrylate compounds and their corresponding acrylates:

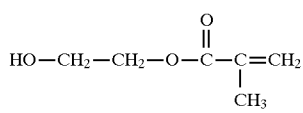

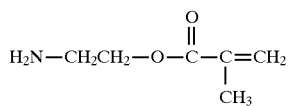

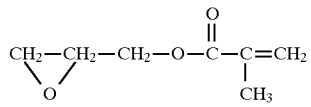

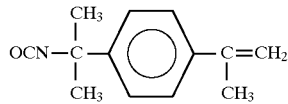

and

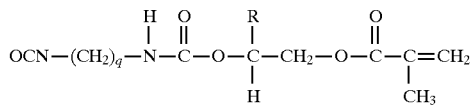

the following allyl compound:

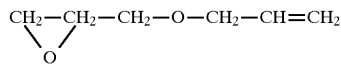

Particularly preferred coupling compounds are the following methacrylate compounds and their corresponding acrylates, wherein R and q are as defined above.

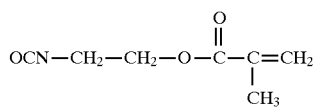

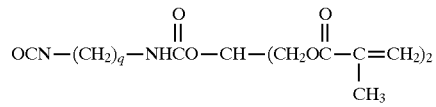

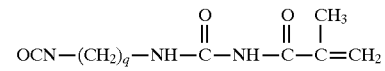

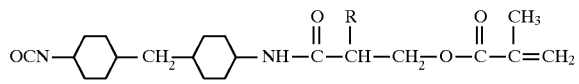

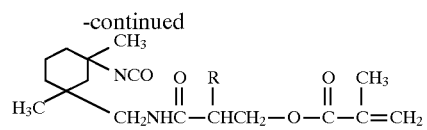

The polymer of the present invention may optionally additionally contain at least one silane moiety that is capable of undergoing a condensation reaction. A condensation reaction is the reaction of two molecules to combine, with the elimination of a third compound. The third compound may be water or, depending on the structure of the specific reactants, this third compound may be an alcohol, amine or any other such compound that is eliminated in the reaction. This silane moiety may, for example, be provided at the time of manufacture of the polymer by coreaction of the A, B and C units described above with a D unit, which is derived from an ethylenically unsaturated monomer copolymerizable with the monomers for A, B and C. This unit has a general formula $$X(Y)_n—Si(R^{12})_iT_j$$

where

X is a vinyl group copolymerizable with the A and B monomers;

Y is a polyvalent linking group (e.g., alkylene, arylene, alkarylene, and aralkylene of 1 to 30 carbon atoms) optionally incorporating heteroatoms e.g. O, N, S, P. Examples are ester, amide, urethane, urea groups.

n is zero or 1;

$R^{12}$ is H or lower alkyl;

i is an integer from 0–2;

j is an integer from 1–3; and i+j=3;

T is a hydroxy or a hydrolyzable group that includes halogen atoms, alkoxy, alkenoxy, acyloxy, carboxy, amino, amido, dialkyliminooxy, ketoxime, aldoxime, and similar groups. Preferably, the hydrolyzable group is selected from the group consisting of alkoxy, alkenoxy, acyloxy, ketoxime and aldoxime. More preferably, the hydrolyzable groups are alkoxy groups such as methoxy and ethoxy, because of their commercial availability, low cost and low toxicity. Examples of such D units include, but not limited to, acrylato- and methacrylato-alkylalkoxysilanes as exemplified by the following formulae.

where, $R^{13}$ is lower alkyl.

Vinylorganoalkoxysilanes such as vinyltrimethoxysilane, vinyltriethoxysilane and vinyl tris(2-methoxyethoxy)silane may also be used in some instances.

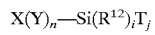

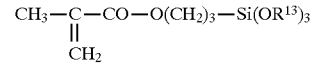

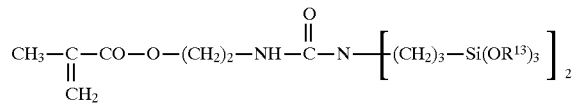

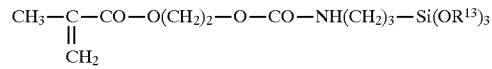

These D unit compounds can be used in their unhydrolyzed, partially hydrolyzed, or fully hydrolyzed form. In the latter two forms, and particularly in the latter form, precautions must be taken to minimize the formation of gels by silane dimerization and oligomerization through siloxane bonds. Any method for this known to those skilled in the art can be used such as careful control of pH or capping of the hydroxyl groups to retard siloxane reactions.

The amount of the D unit silane compound used in the synthesis of the polymer described above preferably is such that the silane moiety is present in 0.1–30 mole percent of the polymer. More preferably, the silane moiety is present in 0.1–20 mole percent of the polymer, and most preferably in 0.1–10 mole percent of the polymer.

Copolymers containing a D unit as described above may be conveniently prepared by copolymerizing the starting monomer units A, B, C and D by standard vinyl polymerization techniques. Alternatively it is possible to modify a fraction of the polar groups of A of a prepared polymer with a compound having at least one silane moiety that is capable of undergoing a condensation reaction, which additionally has a group capable of reacting with the polar group of A.

Preferably, the coating composition contains three components. Component I is the copolymer containing a silane moiety that is capable of undergoing a condensation reaction as described above. Component II is a material having at least two condensation silicone reaction sites that are capable of undergoing a condensation reaction. Component III is optional catalyst to promote the condensation reaction between polymers of Component I and/or between polymers of Component I and compounds of Component II.

Component II is a compound having at least two condensation silicone reaction sites that are capable of undergoing a condensation reaction, and therefore acts as a bridging compound between polymers of Component I in the present system. This component may optionally be a comparatively small molecule, or may be polymeric in nature. Preferably, Component II has a weight average molecular weight between about 64–3000.

Examples of Component II include tetraethyl orthosilicate, and its partially or fully hydrolyzed forms. Preferably, Component II is described by the formula $$Y\text{---}[Si(R^{12})_iT_j]_k$$

where

Y is a polyvalent linking group (e.g., alkylene, arylene, alkarylene, and aralkylene of 1 to 30 carbon atoms) and optionally incorporating heteroatoms e.g. O, N, S, P. Examples are ester, amide, urethane, urea groups.

$R^{12}$ is H or lower alkyl i is an integer from 0–2 j is an integer from 1–3 i+j=3 k=2–50.

T is a hydroxy or a hydrolyzable group that includes halogen atoms, alkoxy, alkenoxy, acyloxy, carboxy, amino, amido, dialkyliminooxy, ketoxime, aldoxime, and similar groups. Preferably, the hydrolyzable group is selected from the group consisting of alkoxy, alkenoxy, acyloxy, ketoxime and aldoxime. More preferably, the hydrolyzable groups are alkoxy groups such as methoxy and ethoxy, because of their commercial availability, low cost and low toxicity.

Examples of Component II are as follows:

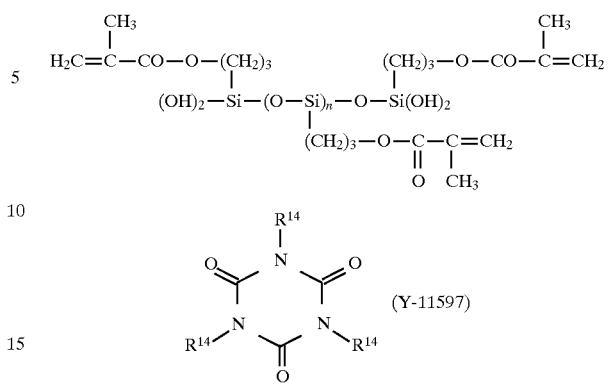

where $R^{14}$=$Si(OCH_3)_3$

Component III is a catalyst that promotes the condensation of the silane moiety that is capable of undergoing a condensation reaction. Moisture generally favors such curing reactions. Any condensation silicone catalysts can be used for this purpose.

Preferred curing catalysts for crosslinking the polymers of the present coatings include the organometallic catalysts containing metals of group III-A, IV-A, V-A, VI-A, VIII-A, I-B, II-B, III-B, IV-B and V-B. Also preferred are the organic amine and organic acid catalysts for the silicone condensation reaction. Particularly preferred catalysts are tin dioctoate, tin naphthenate, dibutyltin dilaurate, dibutyltin diacetate, dibutyltin dioxide, dibutyl tin dioctoate, zirconium chelates, aluminum chelates, aluminum titanates, titanium isopropoxide, triethylene diamine, p-toluene sulfonic acid, n-butyl phosphoric acid, and mixtures thereof.

The combination of components I and III only, in the absence of II, may be sufficient to provide enough crosslinking for a particular application. On the other hand, in certain applications, it may be sufficient to combine components I and II only, particularly when component II is provided in a partially prehydrolyzed form. The speed of cure of the desired application, as well as the actual molecular architecture of the polymer of Component I and the bridging compound of Component II, will dictate the choice of a particular combination of the components of this invention. By judicious choice of solvents and packaging material and delivery system, it is possible to have a one-part or a multi-part system. In the latter case the multiple parts can be mixed just prior to application or can be applied as successive layers.

Polymers containing a silane moiety that is capable of undergoing a condensation reaction may be applied in the same manner as other polymers as described above. For example, these polymers may be applied to a surface of an article before insertion into the mouth, or may be polymerized in situ in the mouth on the oral surface. Coatings may additionally be treated with a surfactant-containing composition for additional benefit.

Coating of surfaces with compositions described herein after placement of orthodontic devices is particularly of interest. Protection of tooth surfaces adjacent to bonded brackets and the like is quite important because good oral hygiene is difficult and the orthodontic devices themselves provide interstices for bacteria, etc. to gather. An important method of use of the present coating materials is application after bonding of orthodontic devices to both the device itself and the tooth surface adjacent to the device.

In the method of the present invention, it is desirable to pretreat the oral surface to be coated with an acid before application of the coating composition. Suitable acids include citric acid, maleic acid, nitric acid, oxalic acid, the acids of phosphorous, sulfur, boron, and the like. Additionally, mildly acidic compositions such as those used to provide fluoride treatments may also be used with benefit as a oral surface pretreatment composition for surface preparation.

When the copolymer is applied as a coating it is generally useful to deliver it in combination with a carrier solvent. This carrier solvent is then removed by suitable means e.g. drying. Examples of carrier solvents include water, ethanol, isopropanol, acetone silicone fluids such as $D_4$, and mixtures thereof. The coating can also be applied in the form of emulsion, e.g. oil-in-water or water-in-oil.

The coatings and surfactant treatments of this invention can be applied as an oral rinse or as a professionally applied coating that can be optionally fixed by further polymerization or cross-linking through ethylenic unsaturations present in the modulating group. The ingredients may also be incorporated into dentrifices such as toothpaste, dental gel, toothpowder, chewing gum, lozenges etc. The coatings and treatments may alternatively be part of a prophy paste or polishing paste that is then applied during a finishing or polishing process with prophy cup, angle, disc etc. They may also be applied by a floss for delivery to interproximal and other difficult to access areas.

For mouthwashes and mouthrinses, the liquid medium which acts as the carrier for the polymer or surfactant may be aqueous or aqueous alcoholic solutions, and optionally may contain other inorganic solvents. A surfactant such as a detergent may be present in polymer delivery compositions.

Toothpastes, gels, chewing gum, lozenges and oral patches used for delivery of either the polymer or the surfactant may additionally contain humectants (such as glycerol, sorbitol, and polyethylene glycol), polishing agents (such as silica, calcium carbonate, and tricalcium phosphate), and thickeners (usually a natural or synthetic gum such as carrageenan, hydroxymethyl cellulose or a synthetic thickener such as fumed silica). A composition is defined to be a paste when the inelastic modulus (otherwise known as "loss modulus") is less than the elastic modulus of the composition. A composition is defined to be a gel when the inelastic modulus is equal to the elastic modulus of the composition. The composition is considered to be "paintable" when it can be applied to the intended substrate using brushes, sponges or other similar applicators conventionally used in the dental arts.

Compositions for delivery of the polymer or surfactant may additionally contain other adjuvants, such as flavorants (both natural and synthetic, such as peppermint oil, menthol and sweeteners), coloring agents, viscosity modifiers, preservatives, antioxidants and antimicrobial agents (such as hydroquinone, BHT, ascorbic acid, p-hydroxybenzoic acid, alkyl esters, sodium sorbate and thymol), other anti-plaque additives (such as organophosphonates, triclosan and others such as those disclosed in U.S. Pat. No. 3,488,419), oral therapeutic agents (such as fluoride salts, chlorhexidine and allantoin), pigments and dyes and buffers to control ionic strength.

The compositions for delivery of the polymer may optionally additionally comprise an ethylenically unsaturated compound. Examples of preferred ethylenically unsaturated compounds are 2,2-bis[4-(2-hydroxy-3-methacryloxypropoxy)phenyl]propane ("BIS-GMA") and 2-hydroxy-ethyl-methacrylate ("HEMA").

Polymers described herein are useful not only for incorporation into toothpastes and the like, but also may be used as external coating compositions for foreign devices to be placed temporarily or permanently in the mouth. For example, these coating compositions may be applied to dental articles that are manufactured outside of the mouth and subsequently placed in the mouth, such as orthodontic brackets, wires, bridges, crowns, dentures and the like. These compositions may be provided either before insertion into the mouth or after insertion by the dental practitioner or by the patient. When these coating compositions are applied to preexisting structure or man-made articles in the mouth, the coating composition may be applied in the form of the polymer or as precursors to the polymer which are in turn polymerized extra-orally or intra-orally by thermal, photo-initiated or redox polymerization. The low frictional coefficients of restorative materials coated by compositions containing these polymers improve the wear resistance of these restorations as compared to restoratives that do not contain these polymers.

When the polymers of the present compositions comprise pendant ethylenically unsaturated moieties that can be reacted in a subsequent step after application to the intended substrate, the compositions also comprise a polymerization catalyst to effect reaction of the ethylenically unsaturated group. Such catalyst may comprise a photoinitiation catalyst or the combination of an oxidizing agent and a reducing agent. Preferably, the initiation agent is appropriate from safety considerations for use in the human body.

The photoinitiator should be capable of promoting free radical crosslinking of the ethylenically unsaturated component on exposure to light of a suitable wavelength and intensity. It also preferably is sufficiently shelf-stable and free of undesirable coloration to permit its storage and use under typical dental conditions. Visible light photoinitiators are preferred. The photoinitiator frequently can be used alone but typically it is used in combination with a suitable donor compound or a suitable accelerator (for example, amines, peroxides, phosphorus compounds, ketones and alpha-diketone compounds).

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzene sulfinate, amines and amine alcohols). Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator should be present in an amount sufficient to provide the desired rate of photopolymerization. This amount will be dependent in part on the light source and the extinction coefficient of the photoinitiator. Typically, the photoinitiator components will be present at a total weight of about 0.01 to about 5%, more preferably from about 0.1 to about 5%, based on the total weight (including water) of the unset coating components.

Alternative polymerization initiators include redox systems, which are a combination of a reducing agent and an oxidizing agent. These agents should react with or otherwise cooperate with one another to produce free-radicals capable of initiating polymerization of the ethylenically-unsaturated moiety. The reducing agent and oxidizing agent preferably are sufficiently shelf-stable and free of undesirable colorization to permit their storage and use under typical dental conditions. They should be sufficiently soluble in or miscible with the carrier medium. The reducing agent and oxidizing agent should be present in amounts sufficient to permit an adequate free-radical reaction rate. Useful reducing agent/oxidizing agent pairs are shown in "Redox Polymerization", G. S. Misra and U. D. N. Bajpai, *Prog. Polym. Sci.,* 8, 61–131 (1982).

Preferred reducing agents include ascorbic acid, cobalt (II) chloride, ferrous chloride, ferrous sulfate, hydrazine, aromatic and aliphatic amines hydroxylamine (depending upon the choice of oxidizing agent) oxalic acid, thiourea, sulfuric acids and salts, and salts of a dithionite or sulfite anion. Preferred oxidizing agents include cobalt (III) chloride, tert-butyl hydroperoxide, ferric chloride, hydroxylamine (depending upon the choice of reducing agent), perboric acid and its salts, and salts of a permanganate or persulfate anion. Hydrogen peroxide can also be used, although it has been found to interfere with the photoinitiator in some instances.

The amount of reducing agent and oxidizing agent should be sufficient to provide the desired degree of polymerization of the ethylenically-unsaturated component. The preferred amount for each of the reducing agent and oxidizing agent is about 0.01 to about 10%, more preferably about 0.02 to about 5%, based on the total weight (including water) of the components. Surfactant treatment, esp. neutral and cationic.

For crosslinkable polymers that are polymerized by a cationic mechanism, suitable intitators include salts that are capable of generating cations such as the diaryliodonium, triarylsulfonium and aryldiazonium salts.

As noted above, it has surprisingly been found that post-treatment of the coatings described herein by a surfactant containing composition provide excellent reduction of adhesion for bacteria or proteinaceous materials. The surfactants may be incorporated at very small amounts in the post-coating composition, and may be either non-ionic or ionic surfactants. Particularly preferred surfactants for use in the post-coating treatment are non-ionic surfactants.

The preferred ionic surfactants include the salts of long-chained aliphatic acids such as sodium dodecylsulfate or sodium octadecyl sulfate. Optionally, the polymer of the coating may contain ionic functionality that acts as the counterion to the surfactant.

The preferred non-ionic surfactants are based on polyhydroxy esters of long chain fatty acids, or polyhydroxy ethers of long chain fatty alcohols. Particularly preferred are polyoxyethylene, sorbitan ethers of long chain fatty acids, e.g. Tween™ 20, 40, 60, or 80 surfactants.

Coatings as described herein may additionally be useful for coating medical articles and articles for use in the medical environment that would benefit from reduced adhesion to surfaces thereof. Examples of such medical articles include devices that are temporarily or permanently implanted in the body, such as pacemakers, blood vessel sieves, bone repair and replacement materials, and the like. Articles that come into contact with body fluids, such as catheters and surgical instruments, also may benefit from being provided with the coating of the present invention. Additionally, articles used for infection control purposes, such as gloves, masks, gowns, drapes and the like, may also benefit from the present coatings.

Substantivity of the coatings of the present invention may be measured by a number of techniques. For example, one may evaluate by chemical means whether or not a coating remains after other types of assault on the coatings. One such analytical means is evaluation of the advancing contact angle using a Wilhelmy Balance as described herein. Preferably, the contact angle is greater than 55° measured against water.

Alternatively, the continued effectiveness of the coating may be evaluated by determining resistance to stain or resistance to bacterial adhesion of a substrate. Resistance of the coating may be evaluated by using a physical assault or a soak assault on the coating. The physical assault may be provided by scrubbing with a brush having a predetermined load for limited periods of time. Alternatively, a physical assault may be provided by repititious grinding or polishing of teeth under a mechanical mechanism used to simulate the action of teeth in the mouth.

Wilhelmy Balance

To evaluate the hydrophobicity and hydrophilicity of the coatings of the present invention, the well-known Wilhelmy Balance technique is used to measure the advancing and receding water contact angles, respectively. This technique is discussed, for example, in "Wettability," John C. Berg, editor, Marcel Dekker, Inc., New York, 1993, pp 11–25. Measurement is taken on a continuous coated sample. All contact angle measurements are done with water.

Preferably, the coatings of the present invention are sufficiently substantive to the intended substrate to provide a water advancing contact angle of at least 55° as measured using the Wilhelmy Balance as described herein for a sample that has been subjected to 2 weeks of soaking in distilled water at 37° C. More preferably, an advancing contact angle of at least 55° is provided on a sample that has been so soaked for three months.

The following examples are given to illustrate, but not limit, the scope of this invention. Unless otherwise indicated, all parts and percentages are by weight, and all molecular weights are weight average molecular weight.

EXAMPLE 1

Iso-butylmethacrylate (14 g), acrylic acid (2 g), ethylenically unsaturated silicone macromer of molecular weight 10,000 prepared according to the procedure for making "monomer C 3b" at column 16 of U.S. Pat. No. 4,693,935 ("PDMS macromer") (4 g) and azobisisobutyronitrile ("AIBN", 0.1 g) were dissolved in iso-propanol. After deoxygenating, the solution was allowed to polymerize at 55° C. The polymer was designated as P1. The solution was then independently coated on etched enamel and dentin. Contact angles were measured by the Wilhelmy balance method using a DCA 322 contact angle analyzer obtained from ATI Instrument, Madison, Wis. Up to 3 cycles were used. Results are shown below:

TABLE 1

| | Contact Angles | | |
|---|---|---|---|
| | Cycle 1 | Cycle 2 | Cycle 3 |
| Control bare etched[1] enamel, polished | | | |
| Advancing | 59 | 45 | 41 |
| Receding | 1.8 | 1.1 | 5.1 |
| Etched enamel, polished, P1 coated | | | |
| Advancing | 107 | 107 | 106 |
| Receding | 71 | 69 | 67 |

TABLE 1-continued

Contact Angles

|  | Cycle 1 | Cycle 2 | Cycle 3 |
|---|---|---|---|
| Above coated enamel slab etched with phosphoric acid | | | |
| Advancing | 105 | 106 | 105 |
| Receding | 67 | 66 | 66 |
| Above coated enamel slab polished (super fine Sof-lex disk ™)[2] | | | |
| Advancing | 104 | 104 | 102 |
| Receding | 57 | 55 | 53 |

[1] Etched with 35% phosphoric acid gel.
[2] Sof-lex polishing disk (3M).

TABLE 2

Contact Angles

|  | Cycle 1 | Cycle 2 | Cycle 3 |
|---|---|---|---|
| Control bare etched enamel | | | |
| advancing | 19 | 33 | 34 |
| receding | 30 | 38 | 39 |
| advancing | 35 | 35 | 36 |
| receding | 39 | 40 | 40 |
| enamel from above etched, P1 coated | | | |
| advancing | 103 | 102 | 102 |
| receding | 67 | 64 | 63 |
| enamel from above wiped with methyl alcohol, etched | | | |
| advancing | 89 | 88 | — |
| receding | 35 | 35 | — |
| enamel from above polished (fine Sof-lex), etched | | | |
| advancing | 80 | — | — |
| receding | 42 | — | — |
| enamel from above polished (medium Sof-lex disk ™), etched | | | |
| advancing | 43 | 34 | 32 |
| receding | 25 | 26 | 26 |

From the above results it is apparent that the coating of the polymer P1 on enamel makes the surface hydrophobic. The coating is not easily lost as noted by the advancing contact angle remaining quite high even after agressive treatments. It is only when it is mechanically abraded away with coarser grades of abrasives that it begins to wear away.

Similar studies were performed after coating a dentin slab with the polymer P1. Results are shown below in table 3.

TABLE 3

|  | Trial 1 | | | Trial 2 | | |
|---|---|---|---|---|---|---|
|  | Cycle 1 | Cycle 2 | Cycle 3 | Cycle 1 | Cycle 2 | Cycle 3 |
| etched bare dentin | | | | | | |
| advancing | 92 | 40 | 40 | 37 | 20 | 25 |
| receding | 8.7 | 8.3 | 7.4 | 20 | 25 | 28 |
| above sample etched, polished | | | | | | |
| advancing | 112 | 108 | 108 | 106 | 98 | 98 |
| receding | 65 | 66 | 66 | 39 | 40 | 40 |
| above coated slab etched with phosphoric acid | | | | | | |
| advancing | 101 | 101 | 100 | 101 | 100 | 70 |
| receding | 54 | 52 | 49 | 46 | 45 | 44 |
| above coated slab then polished (Sof-lex disk ™) | | | | | | |
| advancing | 77 | 60 | 59 | 101 | 100 | 70 |
| receding | 29 | 28 | 27 | 46 | 45 | 44 |

EXAMPLE 2

Iso-butylmethacrylate (13 g), acrylic acid (3 g), PDMS macromer (4 g) and AIBN (0.1 g) were dissolved in THF. After deoxygenating the solution was allowed to polymerize at 55° C. About one-third portion of the carboxylate groups of the resultant polymer were derivatized with isocyanatoethyl methacrylate to provide pendant unsaturated groups. THF was then exchanged with 60 g isopropanol. To a 10 g portion of this solution were added 0.0123 g diphenyliodonium hexafluorophosphate and 0.0031 g of camphorquinone. This polymer is designated as P2. The coating prepared from the polymer was further crosslinked by irradiation with visible light source, Visilux™ 2 from 3M Company.

Results of contact angle study by Wilhelmy balance method are shown in Table 4 below:

TABLE 4

|  | Cycle 1 | Cycle 2 | Cycle 3 |
|---|---|---|---|
| Etched bare enamel | | | |
| advancing | 28 | 38 | 39 |
| receding | 39 | 41 | 42 |
| Etched enamel coated with P2 | | | |
| advancing | 103 | 99 | 99 |
| receding | 22 | 17 | 18 |
| Etched bare dentin | | | |
| advancing | 54 | 36 | 36 |
| receding | 36 | 38 | 38 |
| Etched dentin coated with P2 | | | |
| advancing | 112 | 99 | 97 |
| receding | 61 | 60 | 59 |

The advancing contact angle results show that after treatment with the polymer P2 the hydrophobicity of both the enamel and dentin surfaces increases significantly.

Slabs of Z100 dental composite were coated with P1 or P2. Coating P2 was further crosslinked as described earlier. Contact angles were then measured. The results are given in Table 5 below:

TABLE 5

| | Cycle 1 | Cycle 2 | Cycle 3 |
|---|---|---|---|
| Bare Z100, etched | | | |
| (slab 2) advancing | 63 | 65 | 64 |
| receding | 28 | 28 | 28 |
| (slab 4) advancing | 61 | 64 | 63 |
| receding | 36 | 35 | 35 |
| Etched, P1 coated | | | |
| (slab 2) advancing | 107 | 106 | 106 |
| receding | 68 | 69 | 69 |
| Etched, P2 coated | | | |
| (slab 4) | 106 | 106 | 106 |
| receding | 67 | 67 | 68 |
| Bare, etched, polished Z100 slab | | | |
| (slab 1) advancing | 53 | 52 | 51 |
| receding | 14 | 14 | 14 |
| (slab 3) advancing | 50 | 46 | 48 |
| receding | 22 | 22 | 23 |
| etched, polished Z100 P1 coated | | | |
| (slab 1) advancing | 106 | 107 | 107 |
| receding | 68 | 70 | 71 |
| etched, polished Z100 P2 coated | | | |
| (slab 3) advancing | 105 | 104 | 103 |
| receding | 66 | 65 | 66 |

EXAMPLE 3

Ethyl methacrylate (11.4 g), acrylic acid (2 g), PDMS macromer (4 g) and AIBN (0.1 g) were dissolved in 75 ml of absolute ethanol. The reaction mixture was flushed with nitrogen for 15 minutes and then heated at 55° C. for 8 hours. It was then allowed to cool to room temperature and diluted with an equal volume of isopropanol. This polymer solution was designated as P3.

A slab of bovine enamel was polished with abrasive paper and its contact angle determined in water using the Wilhelmy balance method. The slab was then dried, coated with the solution of P3, air dried, and its contact angle determined again. The values of the control uncoated enamel as well as the coated enamel are shown in Table 6. The experiment was repeated with a slab of bovine dentin; its results are shown in Table 7. A slab of cured Vitremer™ tri-cure glass ionomer was prepared and similarly treated. Results of contact angle on this material before and after coating are shown in Table 8.

TABLE 6

| | Contact Angle | | |
|---|---|---|---|
| Substrate | Cycle 1 | Cycle 2 | Cycle 3 |
| Bare, polished enamel | | | |
| Advancing | 68 | 35 | 35 |
| Receding | 38 | 39 | 39 |
| Polished enamel with P3 | | | |
| Advancing | 99 | 98 | 97 |
| Receding | 59 | 54 | 52 |

TABLE 7

| | Contact Angle | | |
|---|---|---|---|
| Substrate | Cycle 1 | Cycle 2 | Cycle 3 |
| Bare dentin | | | |
| Advancing | 77 | 33 | 34 |
| Receding | 34 | 34 | 34 |
| Dentin coated with P3 | | | |
| Advancing | 103 | 102 | 94 |
| Receding | 62 | 55 | 53 |

TABLE 8

| | Contact Angle | |
|---|---|---|
| Substrate | Cycle 1 | Cycle 2 |
| Vitremer control slab | | |
| Advancing | 70 | 90 |
| Receding | 28 | 27 |
| Vitremer slab coated with P3 | | |
| Advancing | 108 | 108 |
| Receding | 68 | 67 |

From the above data it is apparent that coating with the polymer P3 solution increases the hydrophobicity of the surfaces and that the coating is also retentive.

EXAMPLE 4

Synthesis of polymers A–F

Reagents, as specified in Table 9 were charged into a 3-necked 250 ml round bottom flask fitted with a nitrogen inlet tube, condenser and thermometer. A magnetic stirring bar was placed in the flask and the reagents stirred for 15 minutes with dry nitrogen bubbling briskly through the homogeneous solution. After 15 minutes, the nitrogen flow was reduced and switched from bubbling to blanketing conditions. The solution was heated at 60° C. with stirring, using an oil bath equipped with an electronic temperature controller. Heating was continued for 8 hours. The reaction mixture was then precipitated into water, using 5 ml of water for every ml of polymer solution. The white polymer precipitate was then collected by precipitation, washed with cold water and then dried in a vacuum oven at 70° for several days.

TABLE 9

| polymer | acrylic acid (g) | isobutyl-methacrylate (g) | PDMS macromer (g) | AIBN (g) | THF ml |
|---|---|---|---|---|---|
| A | 1.01 | 15.0 | 2.0 | 0.1 | 54 |
| B | 3.02 | 13.0 | 2.0 | 0.1 | 54 |
| C | 2.02 | 14.0 | 4.0 | 0.1 | 60 |
| D | 1.02 | 15.0 | 6.0 | 0.1 | 66 |
| E | 3.01 | 13.0 | 6.0 | 0.1 | 66 |
| F | 4.00 | 14.0 | 2.0 | 0.1 | 60 |

Preparation of slabs of enamel and dentin
Enamel slab

The labial surface of extracted bovine tooth was ground flat with 120 grit abrasive paper to expose a clean dentin surface free from enamel. This was then polished with 600 grit paper to provide a smooth surface. Using a diamond saw, a thin wafer (about ½ mm) was cut off to include the polished surface. Two such wafers were then glued together with Scotchbond™ Multipurpose (SBMP) dental adhesive system (3M) so that the polished surfaces were facing outwards. The glued sandwich was then cut to give a rectangle of dimensions of about 8 mm×6 mm. A small flat button of a dental composite material was then attached to one of the short sides of the enamel sandwich to provide a handle, using SBMP dental adhesive.

Dentin Slab

The labial surface of a bovine tooth was ground flat with 120 grit abrasive paper to expose a large area of dentin. Using a diamond saw a thin flat slab was sectioned off parallel to the ground surface. The thickness of the slab was about 1 mm. Care was taken to see that the cut surface was dentin only (no visible sign of pulp chamber). The dentin slab was then polished on both flat surfaces with 600 grit paper. A 6 mm×8 mm rectangular section was then cut out with a diamond saw. A small flat button of composite was then glued on to one end (short side) with SBMP.

EXAMPLE 5

Bare enamel slab was first etched with 35% phosphoric acid gel and then polished with 600 grit sand paper. The uncoated slab was tested for contact in water. The slab was then coated with a solution (7.5% polymer in isopropanol) of one of the polymers A–F by dipping for 5 minutes, blotting, followed by air drying. The slab of enamel, coated with polymer was tested for advancing contact angle in water using the Wilhelmy Balance. The coated enamel sample was then stored in deionized water for 2 days and tested again. The sample was then incubated in pooled saliva for 90 minutes, blotted dry and then tested for contact angle. The above sample was then stored in water for 10 minutes and retested. The washed slab, after retesting, was then brushed with a medium bristle tooth brush and then retested for contact angle. The results of advancing contact angle values are shown in Table 10. Advancing contact angle values at the third cycle are reported since at this time equilibrium is attained.

TABLE 10

| STEP | | polymer B | polymer C | polymer E | polymer F | polymer A |
|---|---|---|---|---|---|---|
| | | Adv. contact Angle after third cycle | | | | |
| 1 | Bare enamel etch, polish | 34 | 25 | 28 | 5 | 18 |
| 2 | polymer coated after step 1 | 77 | 89 | 77 | 75 | 75 |
| 3 | water stored after step 2 | 69 | 94 | 74 | 76 | 73 |
| 4 | saliva incubated after step 3 | 25 | 83 | 0 | 58 | 27 |
| 5 | water stored after step 4 | 24 | 83 | 51 | 70 | 0 |
| 6 | brushed after step 5 | 70 | 83 | 62 | 84 | 68 |

The above results indicate that after coating the enamel the tooth surface becomes hydrophobic. The storage in water does not substantially decrease the contact angle, which means the coating is substantive at this point. After incubation with saliva, the salivary proteins and other components stick to some extent on coated surfaces obtained from polymers A, B and E. The saliva treated surface from those polymers are therefore hydrophilic because of adhered proteins and other salivary components. When the saliva treated surface is washed with water (step 5) some of the adherent species from saliva are washed off the surface produced from polymer E. On toothbrushing (step 6), most of the salivary components are removed and the hydrophobic polymer surfaces are re-exposed as manifested by the higher contact angle readings (close to original coated samples). For teeth coated with polymers C and F, not much decrease in contact angle is seen even initially after saliva incubation, thus indicating that adhesion was not favorable to these substrates.

EXAMPLE 6

To show substantivity of coatings, cut enamel or dentin slabs (having no other treatment) were first evaluated for contact angle. These were then independently coated with a solution of polymers B and C at 7.5% concentration by weight as indicated in Table 11 and 12 and dried.

The coated samples were stored for 18 hours in distilled water at 37° C., blotted dry and contact angles were determined. These values are shown in Table 11 and 12.

The samples were then immersed in water and incubated at 37° C. for 1 week and contact angles were determined. These values are shown in Table 11. The contact angle determination was repeated after 2 weeks of incubation, and then again after 3 months of incubation.

Samples were done in replicate. Average of advancing contact angle of the two polymers at the second cycle is reported in Table 11 and Table 12.

TABLE 11

| | Avg. of second cycle adv. contact angle | | | | |
|---|---|---|---|---|---|
| ENAMEL | Initial* | 18 h[1] | 1 wk[1] | 2 wk[1] | 3 mos. |
| polymer B | 45 | 102 | 95 | 89 | 82 |
| polymer C | 52 | 103 | 97 | 83 | 88 |

TABLE 12

| DENTIN | Initial* | 18 h[1] | 1 wk[1] | 2 wk[1] |
|---|---|---|---|---|
| polymer B | 37 | 103 | 95 | 90 |
| polymer C (one sample) | 37 | 105 | 99 | 89 |

*Initial is uncoated substrate
[1]Time of soaking in water at 37° C.

EXAMPLE 7

Effect of pretreatment of enamel or dentin.

The cut and polished enamel or dentin slabs were either (a) etched for 15 seconds with phosphoric acid gel and rinsed with water and dried prior to application of polymer coating or (b) pumiced with Nupro™ coarse polishing paste [enamel slabs polished for 10 min. per side, dentin slabs 4 min. per side], rinsed thoroughly with water and contact angle determined.

The slabs were then coated with polymer C and contact angles determined after 18 h, 1 week and 2 week storage in distilled water at 37° C.

The advancing angle after the second cycle for these experiments are reported in Table 13 and shows that substantivity of the coating is maintained even after prolonged storage.

TABLE 13

| | Initial (uncoated) enamel or dentin | 18 h* | 1 wk* | 2 wk* |
|---|---|---|---|---|
| Enamel acid etched | 48 | 103 | 85 | 83 |
| Enamel pumiced | 34 | 103 | 90 | 79 |
| Dentin acid etched | 22 | 95 | 85 | 67 |
| Dentin pumiced | 40 | 103 | 92 | 82 |

*Time of soaking of coated tooth slab in water at 37° C.

Comparative Example 1

Polydimethylsiloxane polymers containing dimethylpropylamino groups were evaluated for substantivity and hydrophobicity. Two such commercially available polymers were used: PS 510 (molecular weight 2,500) and PS 513 (molecular weight(27,000) from Petrach, Huls.

A 7.5% solution of PS 510 was prepared in acetone. Enamel slabs were coated with this solution followed by drying. Contact angles were then determined.

TABLE 14

| Step | Sample | Adv. Contact angle at 2nd Cycle |
|---|---|---|
| 1 | Cut polished enamel | 51 |
| 2 | Coated after step 1 | 93 |
| 3 | Tooth-brushed after step 2 | 72 |
| 4 | Aged in water 2 weeks after step 3 | 48 |

The decrease in contact angle indicates that the coating was not substantive because hydrophobicity was lost.

Comparative Example 2

Dentin slabs, after cutting and polishing, were coated with a solution of PS 510 (7.5% in acetone) or PS 513 (7.5% in methylethyl ketone). The coated samples were measured for contact angle. These were then aged at 37° C. and the contact angle was measured again. Measurement values are reported in Table 15.

TABLE 15

| contact angle (2nd advancing) | initial (prior to coating) | coated, then 18 h in water @ 37° C. | coated, then 1 wk in water @ 37° C. | coated, then 2 wk in water @ 37° C. |
|---|---|---|---|---|
| PS 510 | 36 | 85 | 84 | 41 |
| PS 513 | 47 | 87 | 65 | 34 |

Loss in contact angle indicates that the coatings were not substantive.

To further evaluate the efficiency of the present coatings, more detailed analysis using biological methodologies were carried out. Biological evaluation generally methods and materials.

Enamel Particles

Enamel particles were produced from approximately 100 bovine teeth by first removing all adherent tissue by scraping with a scapel and a dental curette. The roots were removed with a cutting wheel at the cemento-enamel junction and the pulp removed. The crowns were then immersed in liquid nitrogen for 20 minutes, removed and immediately tapped with a hammer. The dentin was removed from the largest pieces with a grinding wheel. The enamel slabs were then placed in an analytical mill and treated for about 5 minutes at 40° C. The resultant powder was sieved to obtain particles of about 80–120 uM. The particles were washed, treated with acid to clean them and stored dry at 40° C. until used.

Collection/Processing of Saliva Pool

Saliva was collected from volunteers who were asked to chew a 2 inch square of Parafilm for 2–3 minutes and expectorate into a chilled 50 ml tube. The samples were then pooled and centrifuged at 10,000 rpm for 20 minutes at 4° C. The clarified saliva was aliquoted into 10 ml vials and stored at −70° C. until just prior to use.

BIOLOGICAL EVALUATION 1 OF COATINGS

Samples of powdered enamel coated with four polymers were prepared using the polymers A, B, C and E.

These samples were provided for a biological adherence test. Initially, the coated particles were challenged with three materials:

IgG—Immunoglobulin protein PI 7.5
OVA—Ovalbumin protein PI 3.5
P.gin—P-gingivalis bacteria.

Materials and Methods

Fluorescent Labeling of Bacteria

Ten ml of P.gingivalis bacteria at $10^9$/ml in Phosphate Buffered Saline (PBS) were combined with 0.1 ml of Fluorescein Isothiocyanate (FITC) at 1 mg/ml in PBS. The mixture was rotated at room temperature for 1 hour and then washed with 40 ml portions of PBS until the optical density of the supernatant at 495 nm was zero. The dyed bacterial pellet was then resuspended in 10 ml of PBS with 0.1% sodium azide and stored at 4° C. until used.

Coating of Enamel Particles

One hundred and fifty mg of particles (either coated with polymer or not) were combined with 2.5 of human saliva and rotated at room temperature in polypropylene tubes for 1–2 hours. Uncoated particles were rotated at the same time in PBS as controls. The particles were then washed in PBS three times to remove unbound saliva and adjusted to 100 mg/ml in PBS and stored at 4° C. until used.

Adherence Assay

Five mg of particles (in triplicate) were pipetted into the wells of a conical bottom microfilter plate (NUNC) and washed three times with 200 ul of PBS. One hundred ml of either FITC-labeled bacteria, IgG or ovalbumin was added to each well and the plate incubated at room temperature with constant shaking for one hour. The wells were then washed 3 times with 250 ul of PBS and resuspended in 250 ul of the same buffer. Twenty ul portions of the particles were removed and placed in the wells of a IDEXX Assay Plate with a glass fiber filter bottom. The plates were then placed in an IDEXX Screen Machine™, the liquid removed by vacuum filtration and the bound fluorescence determined. After the initial reading the plates were washed twice with PBS containing 0.125% NP-40 and the bound fluorescence redetermined in the Screen Machine™. Results were expressed as relative fluorescent units (RFU).

Results

Particles were tested both with and without polymer coating. Half of each were treated in pooled saliva. These saliva treated particles were then washed with phosphate buffered saline (PBS) and tested for adherence with the non-saliva treated particles. The bound fluorescence was calculated as the percentage of the positive control, i.e. the binding of the bacteria or protein to uncoated enamel particles. The particles were also washed with PBS containing 0.125% NP-40 and bacterial and protein adherence measured.

Figure 3:
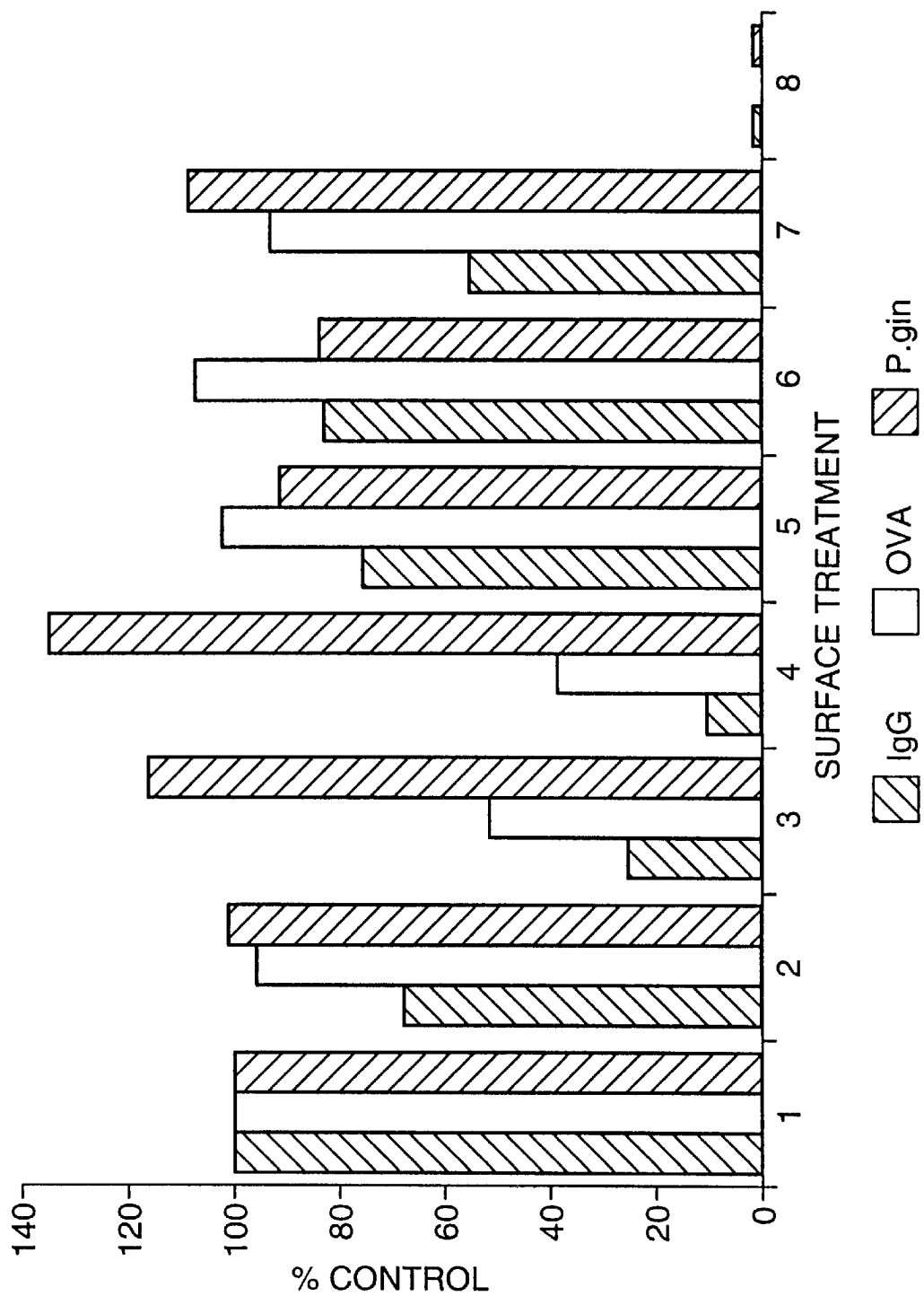
FIG. 3 is a chart showing the relative level of adherence of proteins or bacteria to enamel particles rinsed with phosphate buffered saline.
Figure 4:
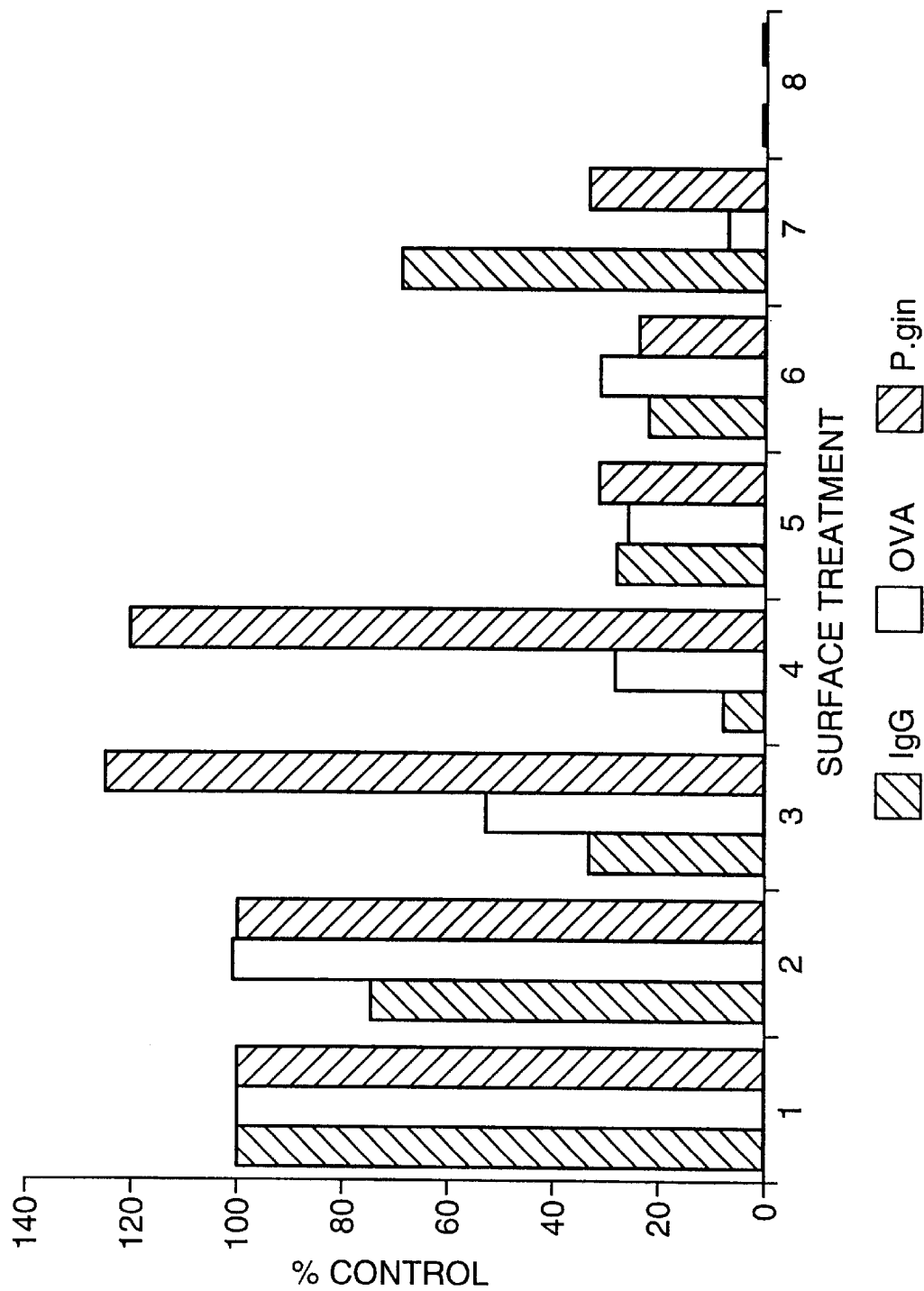
FIG. 4 is a chart showing the relative level of adherence of proteins or bacteria to enamel particles rinsed with an NP-40 surfactant-containing solution.

Results in FIG. 3 are particles rinsed with PBS, those in FIG. 4 are for particles rinsed in PBS+NP-40. Uncoated enamel absorbed large amounts of all three test biologicals (this is 100% on relative scale); coating the enamel with saliva reduced that binding somewhat for IgG but not for OVA and P.gin. Coating the particles with polymer reduced binding substantially, however polymer coated particles supercoated with saliva tended to regain some absorptive properties. Coated particles treated with saliva, then biologicals and washed briefly with PBS containing the non-ionic detergent NP-40 showed substantial decrease of adherence of IgG and OVA for all coatings and P.gin.

BIOLOGICAL EVALUATION 2 OF COATINGS

Growth of Bacterial Strains

Mutans streptococci strains were obtained from the University of Minnesota Dental School (strains 43-2, 43-3 and RL19) as fresh isolates from persons seeking dental care. Additional Mutans Streptococci strains were obtained from the American Type Culture Collection (Strains 10558, 12396, 27351, 27352, 27609 and 33399). All strains were grown in Todd Hewitt Broth in an anaerobic chamber at 37° C. Cells were harvested in late log growth phase and washed three times in sterile filtered saline. The cells were then resuspended at an optical density ("OD") of 1.0 (600 nm) in sterile filtered KCl buffer (0.1M NaCl, 0.05M KCl, 0.1M $MgCl_2$ 0.1 mM potassium phosphate and 1 mM $CaCl_2$, pH 7.0).

Production of Whole Genomic Probes

DNA was isolated from the bacteria using an ASAP™ Kit (Boeringer Manheim) according to the manufacturers directions. Briefly, about $10^9$ cells of the various strains were combined with 2 ml of lysis buffer supplemented with 1 mg/ml Mutanolysin (Sigma). Sixty microliters of heat treated RNAse and 160 μl of lysozyme solution were then added and mixed by gentle inversion. The suspended cells were then incubated at 37° C. for 30 minutes and 100 μl of Proteinase K added. After mixing by gentle inversion, the suspended cells were incubated for 60 minutes at 60° C. Four mililiters of binding buffer was added, mixed by gentle inversion and the entire sample added to a column of DNA binding matrix. The column was drained by gravity and an additional 3 ml of binding buffer added and redrained. One-half milliliter of primary elution buffer was added and the column drained to elute RNA and protein followed by 2 ml of DNA elution buffer which was collected in a 10 mm×100 mm tube. The DNA was then precipitated with isopropanol, washed with ethanol and dried. The resultant pellet of DNA was then dissolved in 50 μl of Tris-EDTA ("TE") buffer and the amount and purity of each preparation determined by optical density at 260/280 nm and electrophoresis on 0.85% TE.

DNA was labeled by nick translation using a GENIUS™ Non-radioactive DNA Labeling Kit (Boeringer Manheim) according to the manufacturers directions. Briefly, 4.5 ug of DNA from each bacterial strain was combined with a balanced mix of hexanucleotides, dNTPs labeled with degoxigenein, the Klenow enzyme and water to 20 ul. The tubes were centrifuged for 10 seconds and incubated overnight at 37° C.

Dot Blot Assays for Adherent Bacteria

Coated and uncoated enamel particles were independently added to 1 ml of saliva and rotated at room temperature for 1 hour. The particles were washed with buffered KCl and 1 ml of bacteria at OD 1.0 (600 nm) added and the mixture rotated at room temperature for an additional hour. The particles were then washed in one of 5 buffer solutions (see below). The particles were then pelleted, 50 μl of DNA extraction buffer added and the suspended particles boiled to extract and solubilize the DNA. The particles were cooled quickly to 40° C., centrifuged and replicate samples of 10 μl for each tube dotted onto a Zeta-Probe™ membrane(Bio Rad). The membranes were then treated with pre-hybridization solution washed and 100 ng of nick translated DNA Probe added in 25 ml of hybridization solution. The hybridization was allowed to incubate at 65° C. overnight before washing three times to remove the unbound probe. The membranes were then incubated in milk blocking solution for 1 hour and goat anti-digoxegenin (1:1000 in blocking buffer) added. After an additional incubation of 1 hour, the membranes were washed to remove unbound antibody and submerged in enzyme substrate solution for 1–2 hours. The reactions were stopped by washing the membrane in EDTA solution and the intensity of the dots estimated by a single observer, using the following scale:

0=no color,

1=just visible,

2=clearly visible circle

3=clearly visible dark circle

4=very dark, highest intensity circle

Washing Experiments to Estimate Strength of Adherence

Five different buffers were prepared for washing experiments: Buffered KCl, Buffered KCl+1% Tween 20, Buffered KCl+1% Tween 80, Buffered KCl+1% soluble toothpaste extract and Buffered KCl+1% mouthwash. Each buffer was used individually as the final wash for the microbial adherence experiments.

Microbial Adherence Experiments

The adherence values for the various combinations of bacteria, plaque resistant coatings and controls can be seen in Table 16. In general, there was an overall reduction of binding of about 25% (range=10–47%) when the enamel coated with all experimental materials were tested and compared to controls in the KCl buffer. Also, there was a substantial reduction, ranging from 81–29%, of binding to the coated particles when the various surfactants or oral products were added to the wash buffer, as compared to untreated enamel controls and a reduction of 86–13% compared to the saliva treated controls. This reduction was greater than can be accounted for by the addition of the various wash solutions alone.

TABLE 16

| Bacterial Strains | ENAMEL TREATMENT | | | | | |
|---|---|---|---|---|---|---|
| | E + B + KCL | E + S + KCL | A1 + S + KCL | B1 + S + KCL | C1 + S + KCL | E1 + S + KCL |
| 43-3 | 2.00 | 1.00 | 2.00 | 1.00 | 1.00 | 0.00 |
| 43-2 | 2.00 | 3.00 | 3.00 | 3.00 | 2.00 | 2.00 |
| RL-19 | 1.00 | 1.00 | 0.00 | 0.00 | 0.00 | 0.00 |
| 10558-432 | 3.00 | 3.00 | 2.00 | 2.00 | 3.00 | 3.00 |

TABLE 16-continued

| Bacterial Strains | ENAMEL TREATMENT | | | | | |
|---|---|---|---|---|---|---|
| 12396-433 | 3.00 | 2.00 | 1.00 | 1.00 | 2.00 | 3.00 |
| 27351 | 2.00 | 3.00 | 0.00 | 3.00 | 3.00 | 2.00 |
| 27352 | 1.00 | 1.00 | 2.00 | 3.00 | 3.00 | 3.00 |
| 27609-new | 2.00 | 1.00 | 0.00 | 0.00 | 0.00 | 0.00 |
| 33399 | 3.00 | 1.00 | 0.00 | 3.00 | 3.00 | 0.00 |
| Average | 2.11 | 1.78 | 1.11 | 1.78 | 1.89 | 1.44 |
| Standard Deviation | 0.78 | 0.97 | 1.17 | 1.30 | 1.27 | 1.42 |

| | E + B + T20 | E + S + T20 | A1 + S + T20 | B1 + S + T20 | C1 + S + T20 | E1 + S + T20 |
|---|---|---|---|---|---|---|
| 43-3 | 1.00 | 2.00 | 0.00 | 0.00 | 0.00 | 0.00 |
| 43-2 | 3.00 | 2.00 | 1.00 | 0.00 | 0.00 | 2.00 |
| RL-19 | 0.00 | 0.00 | 0.00 | 0.00 | 0.00 | 1.00 |
| 10558-432 | 2.00 | 2.00 | 0.00 | 0.00 | 2.00 | 2.00 |
| 12396-433 | 1.00 | 0.00 | 1.00 | 0.00 | 0.00 | 0.00 |
| 27351 | 0.00 | 0.00 | 0.00 | 0.00 | 0.00 | 0.00 |
| 27352 | 0.00 | 0.00 | 0.00 | 0.00 | 0.00 | 0.00 |
| 27609-new | 0.00 | 0.00 | 0.00 | 0.00 | 0.00 | 0.00 |
| 33399 | 0.00 | 0.00 | 3.00 | 0.00 | 0.00 | 3.00 |
| Average | 0.78 | 0.67 | 0.56 | 0.00 | 0.22 | 0.89 |
| Standard Deviation | 1.09 | 1.00 | 1.01 | 0.00 | 0.67 | 1.17 |

| | E + B + T80 | E + S + T80 | A1 + S + T80 | B1 + S + T80 | C1 + S + T80 | E1 + S + T80 |
|---|---|---|---|---|---|---|
| 43-3 | 1.00 | 3.00 | 0.00 | 0.00 | 0.00 | 0.00 |
| 43-2 | 2.00 | 3.00 | 0.00 | 0.00 | 0.00 | 2.00 |
| RL-19 | 1.00 | 0.00 | 0.00 | 0.00 | 3.00 | 0.00 |
| 10558-432 | 3.00 | 3.00 | 0.00 | 0.00 | 3.00 | 3.00 |
| 12396-433 | 3.00 | 3.00 | 0.00 | 0.00 | 0.00 | 0.00 |
| 27351 | 1.00 | 0.00 | 0.00 | 0.00 | 0.00 | 0.00 |
| 27352 | 0.00 | 0.00 | 0.00 | 0.00 | 0.00 | 0.00 |
| 27609-new | 0.00 | 2.00 | 0.00 | 0.00 | 0.00 | 1.00 |
| 33399 | 0.00 | 0.00 | 0.00 | 3.00 | 0.00 | 0.00 |
| Average | 1.22 | 1.56 | 0.00 | 0.33 | 0.67 | 0.67 |
| Standard Deviation | 1.20 | 1.51 | 0.00 | 1.00 | 1.32 | 1.12 |

| | E + B + TP | E + S + TP | A1 + S + TP | B1 + S + TP | C1 + S + TP | E1 + S + TP |
|---|---|---|---|---|---|---|
| 43-3 | 1.00 | 1.00 | 0.00 | 0.00 | 0.00 | 0.00 |
| 43-2 | 3.00 | 3.00 | 0.00 | 0.00 | 0.00 | 0.00 |
| RL-19 | 2.00 | 2.00 | 3.00 | 3.00 | 0.00 | 2.00 |
| 10558-432 | 0.00 | 0.00 | 0.00 | 3.00 | 0.00 | 0.00 |
| 12396-433 | 3.00 | 3.00 | 3.00 | 3.00 | 3.00 | 3.00 |
| 27351 | 3.00 | 3.00 | 0.00 | 4.00 | 0.00 | 3.00 |
| 27352 | 0.00 | 0.00 | 0.00 | 0.00 | 0.00 | 3.00 |
| 27609-new | 2.00 | 3.00 | 0.00 | 0.00 | 0.00 | 3.00 |
| 33399 | 3.00 | 3.00 | 3.00 | 3.00 | 3.00 | 3.00 |
| Average | 1.89 | 2.00 | 1.00 | 1.78 | 0.67 | 1.89 |
| Standard Deviation | 1.27 | 1.32 | 1.50 | 1.72 | 1.32 | 1.45 |

| | E + B + MW | E + S + MW | A1 + S + MW | B1 + S + MW | C1 + S + MW | E1 + S + MW |
|---|---|---|---|---|---|---|
| 43-3 | 0.00 | 2.00 | 0.00 | 0.00 | 0.00 | 2.00 |
| 43-2 | 3.00 | 3.00 | 0.00 | 0.00 | 0.00 | 0.00 |
| RL-19 | 0.00 | 0.00 | 0.00 | 0.00 | 1.00 | 0.00 |
| 10558-432 | 3.00 | 3.00 | 0.00 | 0.00 | 0.00 | 3.00 |
| 12396-433 | 0.00 | 0.00 | 0.00 | 1.00 | 0.00 | 0.00 |
| 27351 | 3.00 | 3.00 | 0.00 | 2.00 | 0.00 | 0.00 |
| 27352 | 0.00 | 3.00 | 0.00 | 0.00 | 0.00 | 0.00 |
| 27609-new | 3.00 | 2.00 | 0.00 | 0.00 | 0.00 | 0.00 |
| 33399 | 1.00 | 2.00 | 0.00 | 1.00 | 0.00 | 0.00 |
| Average | 1.44 | 2.00 | 0.00 | 0.44 | 0.11 | 0.56 |
| Standard Deviation | 1.51 | 1.22 | 0.00 | 0.73 | 0.33 | 1.13 |

KEY:
Enamel Treatments
1st Character - Particle Coating
E = Enamel uncoated by polymer
A1 = Enamel coated with polymer A
B1 = Enamel coated with polymer B
C1 = Enamel coated with polymer C

TABLE 16-continued

| Bacterial Strains | ENAMEL TREATMENT |
| --- | --- |

E1 = Enamel coated with polymer E
2nd Character - Saliva Treatment
B = KCL buffer treatment only
S = Saliva treatment
3rd Character - Wash Buffer
KCL = KCL Buffer wash
T20 = KCL + 1% Tween ™ 20 Buffer wash
T80 = KCL + 1% Tween ™ 80 Buffer wash
TP = KCL + 1% Close-up ™ toothpaste extract wash
MW = KCL + 1% Lavoris ™ mouthwash wash

BIOLOGICAL EVALUATION 3 OF COATING SOLUTIONS

Polystyrene assay wells, previously coated with maleic anhydride, were treated with various solutions as shown below.

i) control, uncoated
ii) coated with a solution of polymer C (7.5% in isopropanol)
iii) coated with a solution of polymer C (7.5% in isopropanol) followed by a rinse consisting of a buffer solution containing 1% by weight of Tween 80
iv) coated with a solution of polymer E (7.5% in isopropanol); or
v) coated with a solution of polymer E (7.5% in isopropanol) followed by a rinse consisting of a buffer solution containing 1% by weight of Tween 80.

An inoculum of S. Challis cells was plated at a concentration of $1 \times 10^7$ cells per well. After the standard washing procedures the cells adhering to the wells were counted in a scintillation counter and expressed as a percentage of the original inoculum. These are reported in Table 17 as a relative percent of the control, uncoated substrate (100%).

TABLE 17

| | Substrate | Retention of Cells |
| --- | --- | --- |
| i) | Control | 100 |
| ii) | Polymer C coated | 60 |
| iii) | Polymer C + rinse | 7 |
| iv) | Polymer E coated | 59 |
| v) | Polymer E + rinse | 15 |

The above results show that application of a polymer coating decreases the adhesion of oral bacteria. Treatment of the coating with a surfactant-containing rinse solution prior to the exposure of the bacteria further reduces the adhesion of the bacteria.

Detailed Description of the Drawing

To compare the coating of tooth slabs with polymer and PDMS solutions. Dentin slabs were coated either with 7.5% solutions of polymer C in isopropanol (Example 4) or with 7.5% solution of PS 510 polydimethyl siloxane in acetone (comparative Example 1). A solution was prepared by dissolving 0.01 grams of methylene blue in 50 ml of distilled water. The coated dentin slabs were immersed in this solution for 5 minutes, then removed and rinsed with distilled water. The slabs were air dried and polaroid photos were taken using an olypus magnifying microscope at 7.5x.

Figure 2:
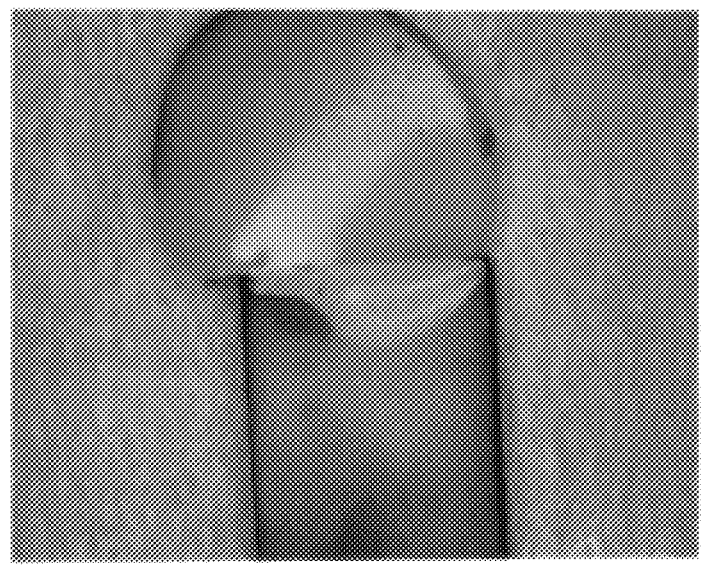
FIG. 2 is a photograph of a tooth chip that has a coating of comparative example 1 of the present invention applied thereto, and which shows retention of a dye to the tooth material.

The dentin slab as shown in FIG. 1 was clear white on both sides indicating that no dye was retained on the dentin slab coated with polymer C. In contrast, FIG. 2 shows that dentin slabs coated with the siloxane of comparative example 1 experienced retention of the dye on the surface of the slabs, as indicated by the dark areas.

As noted in the discussion of the Adherence Assay results of Biological Evaluation 1, FIGS. 3 and 4 show adherence of bacteria to enamel particles having either no coating or a coating as set forth below:

1: Uncoated enamel without saliva treatment
2: Uncoated enamel with saliva treatment
3: Enamel coated with B without saliva treatment
4: Enamel coated with B with saliva treatment
5: Enamel coated with A with saliva treatment
6: Enamel coated with C with saliva treatment
7: Enamel coated with E with saliva treatment
8: Negative control Enamel particles that are provided with coatings show substantial decrease of adhesion of IgG, OVA and/or P.gin.

EXAMPLE 8

Table 18 below describes the reaction compositions of polymers with different A units. Each of the polymers shown in Table 18 was prepared by a continuous feed polymerization process described below.

TABLE 18

| | A Unit | | Advancing Water | Receding Water |
| --- | --- | --- | --- | --- |
| Polymer | Monomer | Weight (g) | Contact Angle | Contact Angle |
| G | Acrylic Acid | 6.00 | 105.50 | 68.27 |
| H | Vinyl-phosphonic Acid | 9.00 | 103.74 | 61.10 |
| I | 2-Hydroxyethyl methacrylate | 10.84 | 103.41 | 54.58 |

To a 250 ml, three-neck, round bottom flask isopropanol (20 ml) was added along with a magnetic stir bar. AIBN (0.2 g) was dissolved in isopropanol (60 ml), and this solution was placed in a 60 ml dropping funnel and attached to the reaction flask. The A unit described in Table 18 along with methyl methacrylate (26 g) and PDMS macromer (4 g) were dissolved in isopropanol (28 ml), placed in a second 60 ml dropping funnel, and attached to the reaction flask. A condenser was placed in the third neck of the reaction flask. At room temperature the reaction vessel was deoxygenated by bubbling nitrogen gas through the feed solutions for 15 minutes. The contents of the two funnels were added to the reaction flask at a steady rate (10 ml/hour) for six hours while maintaining the reaction flask at 60° C. under a nitrogen blanket with mild agitation. Following the complete addition of the monomer and initiator solutions, the reaction flask was maintained at 60° C. and under nitrogen for an additional three hours.

Following the polymerization of polymers G and H, a quantity of acetone sufficient to dissolve the polymers was independently added to each reaction mixture. Each polymer was purified by adding each reaction mixture dropwise to a quantity of water four times that of the total reaction mixture volume with vigorous stirring. Each precipitated polymer was removed from the water mixture, and then dried in a vacuum oven for several days at approximately 60° C. The resultant solid polymers were ground and stored as powders.

Polymer I was used without further purification. The weight percent polymer in the reaction mixture was determined by gravimetric methods, and then the reaction mixture was diluted to approximately 10% polymer in 50/50 isopropanol/acetone.

The hydrophobicity and hydrophilicity of the polymer coatings described in Table 18 were characterized by the advancing and receding contact angles of water, respectively. The advancing and receding contact angles of water were measured using the Wilhelmy plate technique. Polymer-coated glass plates (22 mm×22 mm×0.15 mm) were used as plates for the measurements. The glass plates were silane treated with gamma-methacryloxypropyltrimethoxysilane ("A-174", OSi Specialties, Inc.) prior to dip coating the plates in the polymer solutions. The advancing and receding water contact angles of the coated plates were measured using a plate immersion speed of 50 microns/second. The contact angle results in Table 18, which represent the average of two to three replicate measurements, show that the polymer coatings were more hydrophobic and less hydrophilic than bare, polished enamel (shown in Table 6).

The toothbrush/toothpaste abrasion resistance of the polymers described in Table 18 on enamel was determined using the following procedure termed "Method I". Bovine incisors were potted in an epoxide resin. The buccal surfaces were then polished with 120 and 600 grit silicon carbide wet/dry sand paper to expose clean, flat enamel surfaces. To further clean the polished enamel surfaces, the enamel was acid etched with 10% citric acid in water for 15 seconds, rinsed and dried. The polymers (10%) described in Table 18 were dissolved in the solutions in Table 19 and applied to the polished enamel surfaces with a #75 coating rod from RD Specialties, Inc. The dry polymer films were approximately 5 microns thick.

Each coated enamel surface was brushed with an ORAL B™ 35 Soft Straight toothbrush under a load of 2.7 Newtons at a frequency of 3 cycles/second until only 10% of the enamel remained coated with polymer. The enamel surface and toothbrush were immersed in a slurry of 50/50 by weight CREST™ Regular Flavor toothpaste/distilled water during the brushing process.

At regular intervals during brushing the percentage of the polished enamel surface that remained coated with polymer was determined by a staining procedure. The polished surface was etched with 37% phosphoric acid for one second, rinsed, immersed in a 0.2% aqueous solution of Acid Violet #17 (Aldrich Chemical Company, Inc., Milwaukee, Wis.) for approximately 30 seconds, rinsed, and dried. The plaque resistant polymers were relatively unaffected by the phosphoric acid etching step and were resistant to staining with Acid Violet #17, while the areas where no coating remained on the enamel surface showed staining. The percentage of the polished surface area that remained coated after brushing was determined by visual examination and was reported as the percentage of the surface that was unstained.

Table 19 below shows the comparison of the toothbrush/toothpaste abrasion resistance of polymers G, H and I. The results, which represent the average of five replicate measurements, show that polymers G, H and I have good resistance to abrasion encountered during tooth brushing.

TABLE 19

| Polymer | Coating Solvent | Time to Remove 50% of the Polymer Coating (sec) | Time to Remove 90% of the Polymer Coating (sec) |
|---|---|---|---|
| G | 50/50 iso-propanol/acetone | 250.0 | 398.0 |
| R | 95/5 acetone/ethanol | 246.0 | 532.0 |
| I | 50/50 isopropanol/acetone | 176.0 | 306.0 |

EXAMPLE 9

Table 20 below describes the reaction compositions of plaque resistant polymers with different B units. Each of the polymers in Table 20 was prepared by charging acrylic acid (6 g), PDMS macromer (4 g), AIBN (0.2 g), the described B unit (26 g), and solvent (108 ml) to a 250 ml round bottom flask. At room temperature the reaction mixture was deoxygenated by bubbling nitrogen through the mixture for fifteen minutes. The temperature of the reaction mixture was then raised to 60° C. with mild agitation. The reaction was carried out under a nitrogen blanket for eight hours.

TABLE 20

| | Reaction Composition | | Percentage of Enamel Area that Remained Coated |
|---|---|---|---|
| Polymer | B Unit | Solvent | after Brushing |
| J | iso-Bornyl Methacrylate | Isopropanol | 44.0 |
| K | Methyl Methacrylate | Isopropanol | 76.5 |
| L | tert-Butyl Methacrylate | Tetrahydrofuran | 62.5 |

The polymers J and L were purified by independently adding each reaction mixture dropwise to a quantity of water four times that of the total reaction mixture volume with vigorous stirring. The precipitated polymers were removed from the water mixture, and then dried in a vacuum oven for several days at approximately 60° C. The dried polymers were ground to a fine powder and stored. Polymer K was purified by a similar procedure except that 36 g of acetone was added to the reaction mixture to dissolve the polymer prior to the dropwise addition of the reaction mixture to water.

The toothbrush/toothpaste abrasion resistance of the polymers described in Table 20 on enamel was determined using the following procedure termed "Method II". Bovine incisors were potted in polymethyl methacrylate such that the buccal surfaces were raised above the potting material. The buccal surfaces were then polished with 120 and 600 grit silicon carbide wet/dry sand paper to reveal clean, flat enamel surfaces. To further clean the polished enamel surfaces, the enamel was acid etched with 10% citric acid in water for 15 seconds, rinsed and dried. Solutions of the polymers (10%) described in Table 20 in isopropanol (polymers J and L) or 50/50 isopropanol/acetone (polymer K) were applied to the polished enamel surfaces with a small brush and allowed to air dry. The coated enamel samples were stored at 37° C., 97% relative humidity ("RH") for 24 hours prior to brushing.

Each coated enamel surface was brushed with an ORAL B™ 35 Soft Straight toothbrush under a load of 140 g at a frequency of 50 cycles/minute for fifteen minutes. The enamel surface and toothbrush were immersed in a slurry of 50/50 by weight CREST™ Regular Flavor toothpaste/distilled water during the brushing process.

After brushing, the percentage of the polished enamel surface that remained coated with polymer was determined using the staining procedure described in Method I in Example 8.

Table 20 shows the comparison of the toothbrush/toothpaste abrasion resistance of polymers with various B units. The results, which were the average of two replicates, show that the polymer coatings have good resistance to abrasion encountered during tooth brushing.

EXAMPLE 10

Table 21 below shows the reaction compositions of plaque resistant polymers with different relative amounts of A unit, B unit and C unit. Each polymer in Table 21 was prepared by charging the monomers, AIBN (0.2 g), and isopropanol (108 ml) to a 250 ml three-neck, round bottom flask. At room temperature the reaction mixture was deoxygenated by bubbling nitrogen through the mixture for fifteen minutes. The reaction mixture was then raised to 60° C. with mild agitation. The reaction was carried out under a nitrogen blanket for eight hours.

TABLE 21

| | Reaction Composition | | | | | Time to |
|---|---|---|---|---|---|---|
| Polymer | A Unit Acrylic Acid (g) | B Unit B Methyl Methacrylate (g) | C Unit PDMS Macromer (g) | Advancing Water Contact Angle | Receding Water Contact Angle | Remove the Coating (sec) |
| M | 3.60 | 25.20 | 7.20 | 105.17 | 70.50 | 174 |
| N | 1.98 | 33.22 | 0.80 | 96.67 | 63.75 | 477 |
| K | 6.00 | 26.00 | 4.00 | 100.67 | 71.00 | 412 |
| 0 | 1.98 | 30.02 | 4.00 | 101.33 | 75.25 | 200 |
| P | 6.00 | 29.20 | 0.80 | 98.67 | 67.33 | 173 |

Following the polymerization of the monomers described in Table 21, a quantity of acetone sufficient to dissolve the polymers was added to each reaction mixture. Each polymer was then purified by adding each reaction mixture dropwise to a quantity of water four times that of the total reaction mixture volume with vigorous stirring. The precipitated polymer was removed from the water mixture, and then dried in a vacuum oven for several days at approximately 60° C. The resultant solid polymers were ground and stored as powders.

The hydrophobicity and hydrophilicity of the polymer coatings described in Table 21 were characterized by the advancing and receding contact angles of water, respectively. The advancing and receding contact angles of water were measured using the sessile drop technique. The test specimens for sessile drop contact angle determinations were prepared by first potting bovine incisors in an epoxide resin. The buccal surfaces were then polished with 120 and 600 grit silicon carbide wet/dry sand paper, 6 and 3 micron diamond pastes, and a 0.05 micron alumina slurry to expose clean, flat enamel surfaces. Solutions of the plaque resistant polymers (10%) in Table 21 in 50/50 isopropanol/acetone were applied to the polished enamel surfaces with a small brush. The contact angle results in Table 21, which represent the average of two replicate measurements, show that the polymer coatings were more hydrophobic and less hydrophilic than bare, polished enamel (shown in Table 6).

The toothbrush/toothpaste abrasion resistance of the polymers in Table 21 was measured using Method I except that a #40 coating rod from RD Specialties, Inc. was used to apply the polymer solutions to the prepared enamel surfaces, yielding a dry film thickness of approximately 3 microns. The polymer films were cast from 10% polymer solutions in 50/50 isopropanol/acetone. The teeth were brushed until the polymers were completely removed. The toothbrush/toothpaste abrasion resistance results in Table 21, which represent the average of three to five replicate measurements, show that the polymer coatings have good resistance to abrasion encountered during tooth brushing.

EXAMPLE 11

The adherence of cariogenic bacteria to polymers N and K of Example 10 were determined using the following procedure. Clean bovine teeth were acid etched with 10% citric acid for 15 seconds, rinsed and dried. The crowns of the acid etched teeth were then dip coated into 10% polymer solutions in 50/50 isopropanol/acetone and allowed to air dry.

The polymer coated bovine teeth were placed in 10 mm×30 mm polypropylene test tubes and held in place using 3M™ Imprint™ Impressioning Material (from 3M). The teeth were placed such that only the crown area of the tooth was exposed. The teeth were then placed crown end down into the wells of a 24-well tissue culture plate (Costar, Inc., Cambridge, Mass.) and whole human saliva (2.3 ml) was added to each well to cover the crown. The teeth were incubated one hour with shaking at room temperature. "Mutans streptococci" (American Type Culture Collection, Rockville, Md.) washed in KCl buffer (0.1M NaCl, 0.05M KCl, 1 mM $KH_2PO_4$, 0.1 mM $MgCl_2$, 1 mM $CaCl_2$, pH 7.0) were added to the saliva ($10^9$ per tooth) and incubated an additional two hours at room temperature with shaking. The teeth were then washed twice with either KCl buffer or KCl buffer supplemented with 0.3% TWEEN-80 (Sigma, Inc., St. Louis, Mo.). The teeth were removed from the impressioning material and placed crown end down into new 24-well plates. KCl buffer or KCl buffer with TWEEN-80 (2 ml) was added to each well and the teeth washed twice more. DNA extraction buffer (0.4M NaOH, 10 mM ethylenediaminetetraacetic acid (EDTA)) (2.3 ml) was added to each well and the plates heated to 95°–100° C. for 12 minutes. The solubilized DNA was removed from the wells and divided into three equal portions. Each portion was added to the well of a slot-blot apparatus where the levels of bacterial DNA in each sample were determined. The teeth were then removed from the plates and numbered.

The level of bacterial DNA in each sample was determined using the following DNA slot-blot procedure. A sheet of Zeta-Probe hybridization membrane (BioRad Laboratories, Inc., Richmond, Calif.) was prepared by immersing the membrane in distilled water. The wet membrane was then mounted in a slot-blot apparatus (Minifold II, Schleicher & Schuell, Inc.), vacuum applied and each well rinsed with 0.5 ml of TE buffer (10 mM tris(hydroxymethyl) aminomethane hydrochloride (TRIZMA™ hydrochloride, Sigma, Inc.), 1 mM EDTA, pH 8.0). Solubilized DNA samples were added to each well and washed once with 0.4M NaOH. The vacuum source was disconnected after all liquid had been pulled through the membrane, the apparatus was disassembled and the DNA were immobilized on the semi-dry membrane by exposure to UV light for 3 minutes (StratLinker, Stratagene, Inc., LaJolla, Calif.). The membranes were rinsed briefly in 0.3M NaCl, 0.03M sodium citrate and dried in a 37° C. incubator. The dry membranes were placed in a glass hybridization chamber and 15 ml of pre-hybridization solution (Life Technologies, Inc, Grand Island, N.Y.) added. The tubes were rotated at 65° C. for one hour in the hybridization oven (Hybridizer 700, Stratagene, Inc.). Digoxegenin-labeled whole genomic probes for the organism being tested (150 ng) were added to pre-hybridization solution (15 ml). The diluted probes were boiled for 12 minutes. The pre-hybridization solution was then removed from the glass hybridization chambers and replaced by the diluted probe solution. The slot-blot was incubated overnight at 65° C. with the probe.

The slot-blot membranes incubated overnight with digoxigenin-labeled probes were removed from the hybridization oven and washed twice for 5 minutes in 0.3M NaCl, 0.03M sodium citrate with 0.1% sodium dodecyl sulphate ("SDS") in a glass tray mounted on a shaker platform at room temperature. The membranes were washed twice in 50 ml of 15 mM NaCl, 1.5 mM sodium citrate with 0.1% SDS in the hybridization oven at 65° C. for 30 minutes. The membranes were then placed in a glass tray and washed for 2 minutes at room temperature in maleic acid buffer (0.15M NaCl, 0.1M maleic acid, pH 7.5). The membranes were incubated for 1 hour at room temperature in maleic acid buffer, with 10% skim milk proteins (KPL Laboratories, Gaithersburg, Md.) added, to block nonspecific reactant sites on the membrane. Anti-Digoxigenin antibody labeled with alkaline phosphatase (Boehringer Mannheim, Inc., Indianapolis, Ind.) was diluted 1:5000 in maleic acid buffer with 10% skim milk proteins and added to the membranes for 1 hour at room temperature. The antibody solution was removed and the membrane washed twice for 15 minutes in maleic acid buffer with 0.3% TWEEN-20. After removal of the wash buffer the membrane was equilibrated for 5 minutes in enzyme substrate buffer (0.1M TRIZMA hydrochloride, pH 9.5). Bromochloroindole phosphate/ nitroblue tetrazolium enzyme substrate solution (KPL Laboratories, Inc.) was added and the membrane incubated in the dark at room temperature for 30 minutes. Color development was stopped by transfer of the membrane to TE buffer for 5 minutes followed by soaking in distilled water for 5–10 minutes. The membranes were then placed on paper towels to dry.

Dried membranes were placed on the transport tray of a densitometer (Model 325, Molecular Dynamics, Inc., Sunnyvale, Calif.) and scanned. The data was collected as a digital file using the Molecular Dynamics ImageQuant™ software. The net optical density of each slot was determined and compared to a standard curve of microbial DNA run on each membrane. The microbial equivalents of each slot was calculated and normalized by the tooth crown surface area determined by profilometry techniques.

The bacterial adherence results for polymers N and K are shown in Table 22 for four strains of "mutans streptococci" from the American Type Culture Collection (ATCC), Rockville, Md. Table 22 lists the percent reduction in bound bacteria compared to uncoated enamel. Four species of bacteria were evaluated with and without TWEEN-80 included in the KCl washes. When Tween-80 was included in the KCl washes of the polymer coated teeth, Tween-80 was also included in the KCl washes of the bare enamel control teeth. The results, which represent the average of five measurements, show that when the plaque resistant coatings were applied to enamel, a significant reduction in the binding of cariogenic bacteria was achieved.

TABLE 22

| | Percent Reduction in Adherence of Bacteria Compared to Uncoated Enamel | | | | Percent Reduction in Adherence of Bacteria Compared to Uncoated Enamel/With TWEEN-80 Wash | | | |
|---|---|---|---|---|---|---|---|---|
| Polymer | ATCC 10558 | ATCC 12392 | ATCC 33999 | ATCC 27352 | ATCC 10558 | ATCC 12392 | ATCC 33999 | ATCC 27352 |
| N | 96.84 | 87.41 | 65.45 | 99.80 | 93.69 | 97.49 | 69.09 | 87.41 |
| K | 98.42 | 92.06 | 23.77 | 93.69 | 84.15 | 96.84 | 47.37 | 90.00 |

EXAMPLE 12

Table 23 below describes the reaction compositions of plaque resistant polymers with various D units, including A-174 and the alkoxy-silanes shown below.

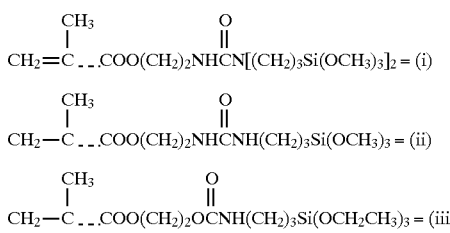

Table 23 also compares a polymer prepared without a D unit. Each of the six polymers in Table 23 was prepared by charging acrylic acid (6 g), iso-butyl methacrylate, PDMS macromer (4 g), the described D unit, AIBN (0.2 g), and isopropanol (108 ml) to a 250 ml round bottom flask. At room temperature the reaction mixture was deoxygenated by bubbling nitrogen through the mixture for fifteen minutes. The reaction mixture was then raised to 60° C. with mild agitation and carried out under a nitrogen blanket for eight hours.

Polymer B was purified by adding the reaction mixture dropwise to a quantity of water four times that of the total reaction mixture volume with vigorous stirring. The precipitated polymer was removed from the water mixture, and then dried in a vacuum oven for several days at approximately 60° C.

The D unit-containing polymers in Table 23 (polymers Q–U) were used without further purification. The weight percent polymer in each reaction mixture was determined by gravimetric methods, and then each reaction mixture was diluted to 10% polymer in isopropanol.

The hydrophobicity and hydrophilicity of the polymer coatings described in Table 23 were characterized by the advancing and receding contact angles of water, respectively. The advancing and receding contact angles of water were measured using the Wilhelmy plate technique, and the results are shown in Table 23. The results, which represent the average of two measurements, show that the polymer coatings were more hydrophobic and less hydrophilic than bare, polished enamel (shown in Table 6).

The toothbrush/toothpaste abrasion resistance of the polymers described in Table 23 on enamel was determined using Method II. Solutions of the polymers (10%) in Table 23 in isopropanol were applied to the polished enamel surfaces with a small brush and allowed to air dry. The samples were stored in a humidity oven at 37° C. for at least 24 hours prior to brushing. The results, which represent the average of at least two measurements, show an increase in the toothbrush/toothpaste abrasion resistance of the polymer coatings with the addition of the D unit.

dibutyl tin dilaurate, or triethylene diamine. The coating solutions were applied to polished enamel surfaces with a small brush and allowed to air dry. The samples were stored in a humidity oven at 37° C. for at least 24 hours prior to brushing. The results, which represent the average of at least two measurements, show that the inclusion of a crosslinkable alkoxy-silane D unit significantly increased abrasion resistance of the coating.

TABLE 24

| Polymer | Advancing Water Contact Angle | Receding Water Contact Angle | Percentage of Enamel Area that Remained Coated After Brushing | | |
|---|---|---|---|---|---|
| | | | Stannous Ocoate | Dibutyl Tin Dilaurate | Triethylene Diamine |
| Q | 103.19 | 80.11 | 84.4 | 12.5 | 85.0 |
| R | 107.30 | 79.76 | 90.0 | 70.0 | 50.0 |
| S | 103.02 | 79.79 | 40.3 | — | — |
| T | 102.55 | 77.91 | 66.3 | — | — |
| U | 102.00 | 79.19 | 60.0 | — | — |

TABLE 23

| Polymer | B Unit iso-Butyl Methacrylate (g) | D Unit Monomer | D Unit Weight (g) | Advancing Water Contact Angle | Receding Water Contact Angle | Percentage of Enamel Area that Remained Coated After Brushing |
|---|---|---|---|---|---|---|
| B | 26.0 | None | 0.00 | 107.82 | 68.45 | 0.0 |
| Q | 24.7 | A-174 | 1.30 | 104.69 | 75.08 | 15.6 |
| R | 23.4 | A-174 | 2.60 | 107.39 | 75.30 | 25.0 |
| S | 24.7 | (i) | 2.60 | 104.50 | 76.38 | 12.5 |
| T | 24.7 | (ii) | 1.75 | 103.52 | 73.70 | 8.0 |
| U | 24.7 | (iii) | 1.97 | 103.38 | 81.33 | 31.0 |

EXAMPLE 13

Table 24 below shows the advancing and receding water contact angles of polymers Q–U of Example 12 when a condensation catalyst was added to the coating solution. The Wilhelmy plate technique was used to determine the contact angles. Stannous octoate was used as the condensation catalyst (5% of the polymer weight). The results in Table 24, which represent the average of two measurements, show that the polymer coatings were more hydrophobic and less hydrophilic than bare, polished enamel (shown in Table 6).

Also shown in Table 24 is the toothbrush/toothpaste abrasion resistance of polymers Q–U on enamel determined using Method II when a condensation catalyst was added to the coating solution (5% by weight of the polymer). Solutions of the plaque resistant polymers (10%) in isopropanol were prepared using condensation catalyst stannous octoate,

EXAMPLE 14

Table 25 below shows the advancing and receding water contact angles of polymers Q and R of Example 12 when a bridging compound for the crosslinking of the D units was added to the coating solution. The bridging compound, termed "PHS", shown in Table 25 was obtained from A-174 after hydrolysis and partial condensation. The concentrations of PHS shown in Table 25 are weight percentages based on the polymer weight in solution. The Wilhelmy plate technique was used to determine the contact angles. The results in Table 25, which represent the average of two measurements, show that the polymer coatings were more hydrophobic and less hydrophilic than bare, polished enamel (shown in Table 6).

TABLE 25

| | Advancing Water Contact Angle | | | Receding Water Contact Angle | | | Percentage of the Enamel Area that Remained Coated after Brushing | | |
|---|---|---|---|---|---|---|---|---|---|
| Polymer | 10% PHS | 20% PHS | 30% PHS | 10% PHS | 20% PHS | 30% PHS | 10% PHS | 20% PHS | 30% PHS |
| Q | 107.34 | 107.47 | 107.19 | 72.3 | 70.49 | 69.78 | 50.0 | 69.0 | 87.5 |
| R | 107.43 | 107.30 | 106.78 | 71.87 | 74.58 | 72.23 | 100.0 | 100.0 | 97.0 |

Tables 26 and 27 below show the advancing and receding water contact angles, respectively, of polymers Q and R of Example 12 when Y-11597 (tris [N-(trimethoxysilyl)propyl] isocyanurate, commercially available from OSi Specialties, Inc.) was added to the coating solution. The amount in moles of this bridging compound added to the coating solution was calculated on the basis of one mole of A-174 unit in the polymer. Tables 26 and 27 also show the effect of a condensation catalyst in conjunction with a bridging compound on the contact angles. The condensation catalyst used was stannous octoate at a concentration of 5% based on the polymer weight in solution. The Wilhelmy plate technique was used to determine the contact angles. The results in Tables 26 and 27, which represent the average of two measurements, show that the polymer coatings were more hydrophobic and less hydrophilic than bare, polished enamel (shown in Table 6).

TABLE 26

Advancing Water Contact Angle

| | No Stannous Octoate | | | With Stannous Octoate | | |
| --- | --- | --- | --- | --- | --- | --- |
| Polymer | 0.5 mole Y-11597 | 1.0 mole Y-11597 | 2.0 mole Y-11597 | 0.5 mole Y-11597 | 1.0 mole Y-11597 | 2.0 mole Y-11597 |
| Q | 107.66 | 107.13 | 107.26 | 107.69 | 107.71 | 107.41 |
| R | 107.53 | 107.64 | 107.85 | 107.66 | 107.53 | 107.13 |

TABLE 27

Receding Water Contact Angle

| | No Stannous Octoate | | | With Stannous Octoate | | |
| --- | --- | --- | --- | --- | --- | --- |
| Polymer | 0.5 mole Y-11597 | 1.0 mole Y-11597 | 2.0 mole Y-11597 | 0.5 mole Y-11597 | 1.0 mole Y-11597 | 2.0 mole Y-11597 |
| Q | 74.87 | 75.73 | 73.31 | 75.76 | 72.97 | 74.26 |
| R | 74.67 | 74.02 | 74.18 | 73.25 | 70.53 | 68.49 |

The toothbrush/toothpaste abrasion resistance of polymers Q and R on enamel determined using Method II when the bridging compound PHS or Y-11597 was added to the coating solution is shown in Tables 25 and 28, respectively. Table 28 also shows the effect of a condensation catalyst in conjunction with a bridging compound. Solutions of the polymers (10%) in isopropanol were prepared with different amounts of the bridging compound and, optionally, with a condensation catalyst. The condensation catalyst used was stannous octoate at a concentration of 5% based on the polymer weight in solution. The coating solutions were applied to polished enamel surfaces with a small brush and allowed to air dry. The samples were stored in a humidity oven at 37° C. for at least 24 hours prior to brushing. The results, which represent the average of at least two measurements, show that the inclusion of a crosslinkable alkoxy-silane D unit significantly increased abrasion resistance of the coating.

TABLE 28

Percentage of the Enamel Area that Remained Coated after Brushing

| | No Stannous Octoate | | | With Stannous Octoate | | |
| --- | --- | --- | --- | --- | --- | --- |
| Polymer | 0.5 mole Y-11597 | 1.0 mole Y-11597 | 2.0 mole Y-11597 | 0.5 mole Y-11597 | 1.0 mole Y-11597 | 2.0 mole Y-11597 |
| Q | 87.5 | 100.0 | 82.5 | 25.0 | 100.0 | 100.0 |
| R | 66.3 | 100.0 | 100.0 | 100.0 | 100.0 | 72.5 |

EXAMPLE 15

The adherence of cariogenic bacteria to the polymers Q and S–U from Example 12 with and without the condensation catalyst stannous octoate (5% based on the polymer weight in solution) were measured using the procedure described in Example 11. The results are shown in Table 29 below for a strain of *Streptococcus sobrinus* (ATCC 27351) and a strain of *Streptococcus gordonii* (ATCC 10558). Table 29 lists the percent reduction in bound bacteria compared to uncoated enamel. Two species of bacteria were evaluated with and without TWEEN-80 included in the KCl washes. When Tween-80 was included in the KCl washes of the polymer coated teeth, Tween-80 was also included in the KCl washes of the bare enamel control teeth. The results, which represent the average of five replicate measurements, show that when the plaque resistant coatings were applied to enamel a significant reduction in the binding of cariogenic bacteria was achieved.

TABLE 29

| Polymer | % Reduction in Adherence of ATCC 27351 | | % Reduction in Adherence of ATCC 10558 | | % Reduction in Adherence of ATCC 27351 with | % Reduction in Adherence of ATCC 10558 with |
|---|---|---|---|---|---|---|
| | No Stannous Octoate | With Stannous Octoate | No Stannous Octoate | With Stannous Octoate | TWEEN-80 With Stannous Octoate | TWEEN-80 With Stannous Octoate |
| Q | 99.23 | 99.99 | 77.92 | 70.04 | 99.30 | 99.46 |
| S | 99.51 | 98.50 | 85.70 | 92.17 | — | — |
| T | 95.10 | 97.77 | 5.19 | 68.79 | — | — |
| U | 94.79 | 87.69 | 87.07 | 86.05 | — | — |

EXAMPLE 16

Table 30 below shows the reaction composition of a polymer with B unit methyl methacrylate and D unit A-174. For comparison, Table 30 contains the reaction composition of a similar polymer prepared without the corresponding D unit. Both polymers shown in Table 30 were prepared by the continuous feed polymerization process described in Example 8. The monomer feeds consisted of acrylic acid (6 g), methyl methacrylate (26 g), PDMS macromer (4 g), and optionally the A-174 D unit (2.6 g) in isopropanol (28 ml). The initiator feed consisted of AIBN (0.2 g) in isopropanol (60 ml). The monomer and initiator feeds were placed in respective 60 ml dropping funnels and the funnels were attached to a 250 ml, three-neck, round bottom flask. A small quantity of isopropanol (20 ml) and a magnetic stir bar were charged to the 250 ml round bottom flask initially. A condenser was placed in the third neck of the reaction flask. At room temperature the reaction vessel was deoxygenated by bubbling nitrogen gas through the feed solutions for 15 minutes. The contents of the two funnels were added to the reaction flask at a steady rate (10 ml/hour) for six hours while maintaining the reaction flask at 60° C. under a nitrogen blanket with mild agitation. Following the complete addition of the monomer and initiator solutions, the reaction flask was maintained at 60° C. and under nitrogen for an additional three hours.

TABLE 30

| Polymer | D Unit Unit | D Unit Weight (g) | Bridging Compound PHS | Condensation Catalyst Stannous Octoate | Advancing Water Contact Angle | Receding Water Contact Angle | Time to Remove 90% of the Polymer Coating (sec) |
|---|---|---|---|---|---|---|---|
| K | None | 0.00 | None | None | 104.47 | 69.02 | 342.5 |
| V 1 | A-174 | 2.60 | None | None | 104.73 | 70.81 | 378.0 |
| 2 | A-174 | 2.60 | 10% or polymer weight | None | 103.32 | 70.84 | 276.0 |
| 3 | A-174 | 2.60 | None | 5% of polymer weight | 103.42 | 71.07 | 1340.0 |

Following the polymerization of polymer K, acetone (50 ml) was added to the reaction mixture to dissolve the polymer. The polymer was then purified by the dropwise addition of the reaction mixture to a quantity of water four times that of the total reaction mixture volume with vigorous stirring. The precipitated polymer was removed from the water mixture, and then dried in a vacuum oven for several days at approximately 60° C. The resultant solid polymer was ground and stored as a powder.

Polymer V was used without further purification. The percent polymer yield was determined by gravimetric methods to be 76.4%. The reaction mixture was then diluted to 10% polymer in 50/50 isopropanol/acetone.

Table 30 also shows the advancing and receding water contact angles of polymer K and polymer V with and without the bridging compound PHS and the condensation catalyst stannous octoate. The contact angles were measured using the Wilhelmy plate technique. The results, which represent the average of two measurements, show that the polymer coatings were more hydrophobic and less hydrophilic than bare, polished enamel (shown in Table 6).

The toothbrush/toothpaste abrasion resistance of polymer K, and polymer with and without the bridging compound PHS and the condensation catalyst stannous octoate on enamel was determined using Method I. Solutions of the polymers (10%) described in Table 30 in 50/50 isopropanol/acetone were applied to the polished enamel surfaces with a #75 coating rod. The dry polymer films were approximately 5 microns thick. The coated teeth were stored in a humidity oven at 37° C. for 70 hours at 95% RH prior to tooth brushing. The coated teeth were brushed until only 10% of the enamel remained coated with polymer. The results in Table 30, which represent the average for five replicate measurements, show that the inclusion of a crosslinkable alkoxy-silane D unit significantly increased the abrasion resistance of the coating.

What is claimed:

1. A coating on hard tissue surfaces or surfaces of the oral environment, which coating is made from a polymer comprising repeating units
   A) 1–80% by weight of a polar or protected polar groups group
   B) 0–98% by weight of a group containing functionalites that modulate a property selected from the group consisting of glass transition temperature, solubility in the carrier medium and hydrophilic-hydrophobic balance,
   C) 1–40% by weight of a graft polysiloxane chain having molecular weight of at least 500,
wherein said polymer contains at least one silane moiety that is capable of undergoing a condensation reaction.

2. The coating of claim 1, wherein the silane moiety is present in 0.1–30 mole percent of the polymer.

3. The coating of claim 1, wherein the silane moiety has the formula

where
   $R^{12}$ is H or lower alkyl;
   i is an integer from 0–2;
   j is an integer from 1–3;
   i+j=3; and
   T is hydroxy or a hydrolyzable group selected from the group consisting of halogen atoms, alkoxy, alkenoxy, acyloxy, carboxy, amino, amido, dialkyliminooxy, ketoxime, and aldoxime.

4. The coating of claim 1, said polymer comprising repeating units
   A) 1–80% by weight of a polar or protected polar groups group
   B) 0–98% by weight of a group containing functionalities that modulate a property selected from the group consisting of glass transition temperature, solubility in the carrier medium and hydrophilic-hydrophobic balance,
   C) 1–40% by weight of a graft polysiloxane chain having molecular weight of at least 500,
   D) 1–50% by weight of a group having the formula
   $X(Y)_n$—$Si(R^{12})_i T_j$
where
   X is a vinyl group copolymerizable with the A and B monomers;
   Y is a polyvalent linking group;
   n is zero or 1;
   $R^{12}$ is H or lower alkyl;
   i is an integer from 0–2;
   j is an integer from 1–3;
   i+j=3; and
   T is a hydroxy or a hydrolyzable group selected from the group consisting of halogen atoms, alkoxy, alkenoxy, acyloxy, carboxy, amino, amido, dialkyliminooxy, ketoxime aldoxime.

5. The coating of claim 4, wherein T is selected from the group consisting of alkoxy, alkenoxy, acyloxy, ketoxime and aldoxime.

6. The coating of claim 4, wherein T is an alkoxy group.

7. The coating of claim 1, said coating additionally comprising a catalyst that promotes the condensation of reactive silane moieties.

8. The coating of claim 7, wherein said catalyst is selected from the group consisting of organometallic catalysts containing metals of group III-A, IV-A, V-A, VI-A, VIII-A, I-B, II-B, III-B, IV-B and V-B.

9. The coating of claim 8, wherein said catalyst is selected from the group consisting of tin dioctoate, tin naphthenate, dibutyltin dilaurate, dibutyltin diacetate, dibutyltin dioxide, dibutyl tin dioctoate, zirconium chelates, aluminum chelates, aluminum titanates, titanium isopropoxide and mixtures thereof.

10. The coating of claim 7, wherein said catalyst is selected from the group consisting of triethylene diamine, p-toluene sulfonic acid, n-butyl phosphoric acid, and mixtures thereof.

11. The coating of claim 1, said coating additionally comprising a compound comprising at least two condensation silicone reaction sites that are capable of undergoing a condensation reaction.

12. The coating of claim 11, wherein said compound has the formula

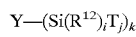

where
   Y is a polyvalent linking group;
   $R^{12}$ is H or lower alkyl;
   i is an integer from 0–2;
   j is an integer from 1–3;
   i+j=3;
   k=2–50; and
   T is a hydroxy or a hydrolyzable group selected from the group consisting of halogen atoms, alkoxy, alkenoxy, acyloxy, carboxy, amino, amido, dialkyliminooxy, ketoxime and aldoxime.

13. The coating of claim 12, wherein T is selected from the group consisting of alkoxy, alkenoxy, acyloxy, ketoxime and aldoxime.

14. The coating of claim 12, wherein T is an alkoxy group.

15. The coating of claim 11, wherein said compound is the product of hydrolysis and partial condensation of gamma-methacryloxypropyl trimethyloxy silane.

16. The coating of claim 11, wherein said compound has the formula

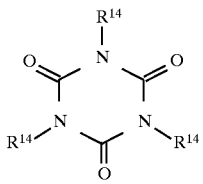

wherein $R^{14}$ is —$(CH_2)_3$—$Si(OCH_3)_3$.

17. The coating of claim 11, said coating additionally comprising a catalyst that promotes the condensation of reactive silane moieties.

18. The coating of claim 17, wherein said catalyst is selected from the group consisting of organometallic catalysts containing metals of group III-A, IV-A, V-A, VI-A, VIII-A, I-B, II-B, III-B, IV-B and V-B.

19. The coating of claim 18, wherein said catalyst is selected from the group consisting of tin dioctoate, tin naphthenate, dibutyltin dilaurate, dibutyltin diacetate, dibutyltin dioxide, dibutyl tin dioctoate, zirconium chelates, aluminum chelates, aluminum titanates, titanium isopropoxide and mixtures thereof.

20. The coating of claim 17, wherein said catalyst is selected from the group consisting of triethylene diamine, p-toluene sulfonic acid, n-butyl phosphoric acid, and mixtures thereof.

* * * * *

UNITED STATES PATENT AND TRADEMARK OFFICE
CERTIFICATE OF CORRECTION

PATENT NO.: 5,866,630
DATED: February 2, 1999
INVENTOR(S): Sumita B. Mitra, Sharon M. Rozzi and Brant L. Kedrowski It is certified that error appears in the above-identified patent and that said Letters Patent is hereby corrected as shown below:

Front page, List of Inventors, "Charles E. Shelburne" should be removed from the list of inventors.

Signed and Sealed this

Seventeenth Day of April, 2001

*Attest:*

NICHOLAS P. GODICI

*Attesting Officer*    Acting Director of the United States Patent and Trademark Office